US006896899B2

(12) United States Patent
Demopolos et al.

(10) Patent No.: US 6,896,899 B2
(45) Date of Patent: May 24, 2005

(54) PHARMACEUTICAL PREPARATIONS OF GLUTATHIONE AND METHODS OF ADMINISTRATION THEREOF

(75) Inventors: Harry B. Demopolos, Scarsdale, NY (US); Myron L. Seligman, Pleasantville, NY (US)

(73) Assignee: Antioxidant Pharmaceuticals Corp., Elmsford, NY (US)

( * ) Notice: Subject to any disclaimer, the term of this patent is extended or adjusted under 35 U.S.C. 154(b) by 361 days.

(21) Appl. No.: 10/083,327

(22) Filed: Feb. 25, 2002

(65) Prior Publication Data

US 2002/0136763 A1 Sep. 26, 2002

Related U.S. Application Data

(63) Continuation of application No. 09/331,947, filed as application No. PCT/US97/23879 on Dec. 31, 1997, now Pat. No. 6,350,467.
(60) Provisional application No. 60/034,101, filed on Dec. 31, 1996.

(51) Int. Cl.[7] ............................ A61K 9/48; A61K 31/00

(52) U.S. Cl. ..................... 424/451; 456/489; 514/18; 514/21

(58) Field of Search ................................ 424/464, 451, 424/489, 456, 465

(56) References Cited

U.S. PATENT DOCUMENTS

| 4,871,528 A | * 10/1989 | Tognella et al. | 424/649 |
| 5,780,440 A | * 7/1998 | Lezdey et al. | 514/21 |
| 6,586,404 B1 | * 7/2003 | Demopolos et al. | 514/18 |

OTHER PUBLICATIONS

Aruga, et al., "Kinetic studies on the decomposition of glutathione. I. Decomposition in solid state", Chem. Pharm. Bull, 26:2081–91, 1978.
Aruga, et al., "Kinetic studies on decomposition of glutathione. II. Anaerobic decomposition in aqueous solution", Chem. Pharm. Bull, 28:514–20, 1980.
Lash, et al., "Distribution of oxidized and reduced forms of glutathione and cysteine in rat plasma", Arch. Biochem. Biophys, 240:583–92, 1985.
Meister, A., "Selective modification of glutathione metabolism", Science 220: 472–477, 1983.
Meister, et al., "Glutathione", Ann. Rev. Biochem, 72: 711–60, 1983.
Riley, et al., "A comparative study of the toxicity of chemically reactive xenobiotics . . . ", J. Pharmacol. 45(4): 263–267, 1993.
Wierzbicka, et al., "Glutathione in food" J. Food Comp. Anal. 2:327–337, 1989.
Bravenboer, et al., "Potential use of glutathione for the prevention and treatment of diabetic neuropathy in the streptozocin–induced diabetic rat", Diabetologia 35:813–17, 1992.
Cavaletti, et al., "Comparison of reduced glutathione with 2–mercaptoethane sulfonate to prevent cyclophosphamide–induced urotoxicity", Cancer Letters 32:1, 1986.
Hamers, et al., "Reduced glutathione protects against cis-platin–induced neurotoxicity in rats", Cancer Res. 53: 544–549, 1993.

(Continued)

Primary Examiner—James M. Spear
(74) Attorney, Agent, or Firm—Milde & Hoffberg LLP

(57) ABSTRACT

A method of increasing glutathione levels in mammalian cells comprising administering an oral bolus of encapsulated pharmaceutically stabilized glutathione in a rapidly dissolving formulation to a mammal on an empty stomach. Pharmaceutical formulations including glutathione are also disclosed.

25 Claims, 2 Drawing Sheets

2 grams/day
GSH in PBMCs, Patient G

OTHER PUBLICATIONS

Novi, et al., "Glutathione and aflatoxin $B_1$–induced liver tumors: . . . ", Ann. NY Acad. XCI., 397:62–71, 1982.

Skoulis, et al., "Depression of hepatic glutathione by opioid analgesic drugs in mice", Toxicol. Appl. Pharmacol. 99:139–47, 1989.

Villani, et al., "Prevention of doxorubicin–induced cardiomyopathy by reduced glutathions", Cancer Chemother. Pharmacol., 28:365–369, 1991.

Wagner, et al., "Lack of effect of long–term glutathione administration on aflatoxin B1–induced hepatome in male rats", Chem. Biol. Interactions, 53:57–68, 1985.

Yoda, et al., "Prevention of Doxorubicin myocardial toxicity in mice by reduced glutathione", Cancer Research, 46:2551, 1986.

Droge, et al., Glutathione augments the activation of cytotoxic T lymphocytes in vivo, Immunobiol, 172:151–156, 1986.

Furukawa, et al., "Reversal of age–associated decline in immune responsiveness by dietary glutathione supplementation in mice", Mech. Ageing Dev. 38:107–117, 1987.

Franklin, et al., "Glutathione augments in vitro proliferative responses of lymphocytes to concanavalin A to a greater degree in old than in young rats", J. Nutr. 120:1710–17, 1990.

Kavanaugh, et al., "Proliferative capacity of human peripheral lymphocytes sorted on the basis of glutathione content", J. Cell. Physiol. 145:472–80, 1990.

Robinson, et al., "Glutathione depletion in rats impairs T–cell and macrophage immune function", Arch. Surg. 128:29–35, 1993.

Suthanthiran, et al., "Glutathione regulates activation–dependent DNA synthesis . . . ", Proc. Natl. Acad. Sci. USA 87:3343–3347, 1990.

Schreck, et al., "Reactive oxygen intermediates as apparently widely used messengers in the activation of the NF–kappa B . . . " EMBO J 10:2247–2258 (1991).

Arpadi, et al., Glutathione deficiency in HIV–1–infected children with growth failure (submitted for publication).

Baruchel, et al., "The role of oxidative stress in disease progression in individuals infected by the human immunodeficiency virus", J. Leukocyte Biol. 52:111–114, 1992.

Buhl, et al., "Systemic glutathione deficiency in symptom–free HIV–seropositive individuals", Lancet ii:1294–1298, 1989.

Droge, et al., "HIV–induced cysteine deficiency and T–cell dysfunction–a rationale for treatment with N–acetylcysteine", Immunol. Today 13:211–4, 1992.

Eck, et al., "Low concentrations of acid–soluble thiol (cysteine) in the blood plasma of H1V–1–infected patients", Biol. Chem. Hoppe–Seyler 370:101–108, 1989.

Fauci, A.S., "Multifactorial nature of human imrnunodeficiency virus disease: Implications for therapy", Science 262:1011–1018, 1993.

Foley, et al., HIV infection of monocytes inhibits the T–lymphocyte proliferative response to recall antigens via productions of eicosanoids, Immunology 75:391–97, 1992.

Hasan, et al., "Stimulation of human T–cell clone with anti–CD3 or tumor necrosis factor induces NfkB . . . ", Proc. Natl. ACAD. XCI, 87:7861–65, 1990.

Ho, et al., Glutathione and N–acetylcysteine suppression of human immunodeficiency virus replication . . . , AIDS Res. Hum. Retroviruses, 8:1249–53, 1992.

Israel, et al., "Redox status of cells influences constitutive or induced NF?B translocation . . . ", J. Immunol 149:3386–93, 1992.

Kalebic, et al., "Suppression of human immunodeficiency virus expression in chronically infected monocytic cells . . . ", Proc. Natl. Acad. XCI. USA 87:986–990, 1991.

Le Grand–Poels, et al., "Activation of human immunodeficiency virus type 1 by oxidative stress", AIDS Res. Hum. Retrov. 6:1389–97, 1990.

Mihm, et al., Inhibition of H1V–1 replication and NF–kb activity by cysteine and cysteine derivatives, AIDS 5:497–503, 1991.

National Institutes of Health, Dr. Howard C. Greenspan, Chairman of Conference on Free Radicals and Antioxidants in HIV/AIDS, Nov. 12–13, 1993/Greenspan, H.C. The role of reactive oxygen species, antioxidants and phytopharmaceuticals in human immunodeficiency virus activity, Med–Hypotheses 40:85–92, 1993.

Roederer, et al., "N–acetylcysteine inhibits latent HIV expression in chronically infected cells", AIDS Res. Human Retrovir. 7:(6) 563–567, 1991.

Roederer, et al., "CD4 and CD8 T cells with high intracellular glutathione levels are selectively lost as the HIV infection progresses", Internat. Immunol. 3:933–37, 1991.

Roederer, et al., Cytokine–stimulated human immunodeficiency virus replication is inhibited by N–acetyl–L–cysteine, Proc. Natl. Acad. Sci USA 87:4884–4888, 1990.

Staal, et al., "Intracellular thiols regulate activation of nuclear factor kapp–B . . . ", Proc. Natl. Acad. SCI USA 87:9943–9947, 1990.

Staal, et al., "Glutathione deficiency and human immunodeficiency virus infection", Lancet 339:909–12, 1992.

Staal, et al., "Intracellular glutathione levels in T cell subsets decrease in HIV–infected individuals", AIDS Res. Hum. Retroviruses 8:305–11, 1992.

Staal, et al., "Antioxidants inhibit stimulation of HIV transcription", AIDS Res. Hum. Retrov. 9:299–306, 1993.

Wahl, et al., "Human immunodeficiency virus glycoprotein (gp120) induction of monocyte arachidonic acid metabolites . . . ", Proc. Natl. Acad. Sci. 86:621–625, 1989.

Ceriello, et al., "Anti–oxidants show an anti–hypertensive effect in diabetic and hypertensive subjects", Clin. Sci. 81:739–742, 1991.

Paolisso, et al., "Glutathione infusion potentiates glucose–induced insulin secretion in aged patients with impaired glucose tolerance", Diabetes Care 15:1–7, 1992.

Sen, et al., "Antioxidant and redox regulation of gene transcription", FASEB J. 10, 709–720 1996.

Makino, et al., Cross–Talk between Endocrine Control of Stress Response and Cellular Antioxidant Defense System, Thioredoxin is a Redox–Regulating Cellular Cofactor for Glucocorticoid Hormone Action (Poster), Proceedings of 3rd Internet World Congress on Biomedical Sciences, 1996.12.9–20 Riken, Tsukuba, Japan.

Kuehl, et al., "Studies on a destructive oxidant released in the enzymatic reduction of prostaglandin G2 and other hydroperoxy acids", In:Pathology of Oxygen, ed. A.P. Auton, Acad. Press, New York, 1982, pp. 175–190.

Lash, et al., "Exogenous glutathione protects intestinal epithelial cells from oxidative injury", Proc. Natl. Acad. Sci. USA 83:4641–4645, 1986.

Okamoto, et al., Oxygen Radicals, Redox Regulation of the NF–kB Signaling and Disease Control by Antioxidants (poster), Proceedings of 3rd Internet World Congress on Biomedical Sciences, 1996.12.9–20 Riken, Tsukuba, Japan.

Ginn–Pease, et al., "Redox signals and NF–kappaB activation in T cells", Free Radic Biol Med. 1998 Aug;25(3):346–61.

Holmgren, A., "Thioredoxin and glutaredoxin systems", J Biol Chem 1989; 264, 13963–13966.

Sugita, et al., "Pigment epithelium–derived factor (PEDF) has direct effects on the metabolism and proliferation of microglia . . . ", J Neurosci Res Sep 15, 1997;49(6):710–8.

Esposito, et al., "Inhibition of the differentiation of human myeloid cell lines by redox changes induced through glutathione depletion", Biochem. J. (1994) 301, 649–653.

Alberdi, E., et al., "Binding of Pigment Epithelium–derived Factor (PEDF) to Retinoblastoma Cells . . . ", J Biol Chem. Oct 29, 1999;274(44):31605–31612.

Dawson, D.W., et al., "Pigment epithelium–derived factor: a potent inhibitor of angiogenesis", Science. Jul 9, 1999;285(5425):245–8.

Tombran–Tink, J., et al., "Organization, evolutionary conservation, expression and unusual Alu density of the human gene . . . , "Mol Vis. Nov 4, 1996;2:11.

Goliath, R., et al., "The gene for PEDF, a retinal growth factor is a prime candidate for retinitis pigmentosa . . . ", Mol Vis. Jun 19, 1996;2:5.

Bohm, et al., "A feasibility study of cisplatin administration with low–volume hydration and glutathione protection . . . ", Anticancer Res. 11:1613–1616, 1991.

Cozzaglio, L., et al., "A feasibility study of high–dose cisplatin and 5–fluorouracil with glutathione protection . . . ", Tumori 76:590–594, 1990.

Dei Re, F., et al., "Efficacy and safety of high–dose cisplatin and cyclophosphamide with glutathione protection . . . ", Cancer Chemother. Pharmacol. 25:355–360, 1990.

Nobile, M.T., et al., "A preliminary clinical study of cyclophosphamide with reduced glutathione as uroprotector", Tumori 75:257–258, 1989.

Costagliola, C., et al., Anemia and chronic renal failure: a therapeutic approach by reduced glutathione parenteral administration, Nephron 61:404–408, 1992.

Dalhoff, K., et al., "Glutathione treatment of hepatocellular carcinoma", Liver 12:341–343, 1992.

Dekant, W., "Bioactivation of nephrotoxins and renal carcinogens by glutathione S– conjugate formation", Toxicol. Letters 67:151–60, 1993.

Domingo, J.L., et al., "Chelating agents in the treatment of acute vanadyl sulphate intoxication in mice", Toxicology 62:203–211, 1990.

Martensson, J., et al., "Glutathione ester delays the onset of scurvy in ascorbate– deficient guinea pigs", Proc. Nat. Acad. Sci. USA 90:317–321, 1993.

Thust, R., et al., "Exogenous glutathione induces sister chromatid exchanges, clastogenicity and endoreduplication . . . ", Cell Biol. Toxicol. 1:123–31, 1985.

Aebi, S., et al., "Divergent effects of intravenous GSH and cysteine on renal and hepatic GSH.", Aer. J. Physiol. 263(2 pt 2):R348–R352, 1992.

Ammon, H.P.T., et al., "Pharmacokinetics of intravenously administered glutathione in the rat", J. Pharm. Pharmacol. 38:721–725, 1986.

Anderson, M.E., et al., "Glutathione monoethyl ester: Preparation, uptake by tissues, and conversion to glutathione", Arch. Biochem. Biophys. 239:538–548, 1985.

Aw, T.Y., et al., "Oral glutathione increases tissue glutathione in vivo", Chem. Biol. Interact. 80:89–97, 1991.

Borok, Z., et al., "Effect of glutathione aerosol on oxidant–antioxidant imbalance in idiopathic pulmonary fibrosis", The Lancet 338:215–216, 1991.

Buhl, R., et al., "Augmentation of glutathione in the fluid lining the epithelium of the lower respiratory tract . . . ", Proc. Natl. Acad. Sci.USA 87: 4063–4067, 1990.

Bump, E.A., et al., "Elevation of mouse kidney thiol content following administration of glutathione", Radiother. Oncol. 23:21–25, 1992.

Griffith, O.W., et al., "Formation of g–glutamyl–cyst(e)ine in vivo is catalyzed by g–glutamyl transpeptidase", Proc. Natl. Acad. Sci. USA 78:2777–2781, 1981.

Hagen, T.M., et al., "Fate of dietary glutathione. Disposition in the gastrointestinal tract", Am. J. Physiol. 259: G530–G535, 1990.

Hagen, T.M., et al., "Transepithelial transport of glutathione in vascularly perfused small intestine of rat", Am. J. Physiol. 252:G607–G613, 1987.

Hagen, T.M., et al., "Bioavailability of dietary glutathione. Effect on plasma concentration", Am. J. Physiol. 259:G524–G529, 1990.

Hahn, R., et al., "The fate of extracellular glutathione in the rat", Biochim. Biophys. Acta 539:324–337, 1978.

Puri, R.N., et al., "Transport of glutathione, as g–glutamyl-cysteinylglycyl ester, into liver and kidney", Proc. Natl. Acad. Sci. USA 80:5258–5260, 1983.

Vina, J., et al., "Effect of oral glutathione on hepatic glutathione levels in rats and mice", Brit. J. Nutr. 62:683–91, 1989.

Aebi, S., et al., "High–dose intravenous glutathione in man. Pharmacokinetics and effects on cyst(e)ine levels in plasma and urine", Eur. J. Clin. Invest. 21:103–110, 1991.

Hagen, T.M., et al., "Role of glutathione transport in extrahepatic detoxication. in Glutathione Centennial: Molecular Perspectives and Clinical Implications", N. Taniguchi, T. Higashi, Y. Sakamoto and A. Meister, eds. Acad. Press, New York, 1990.

Jones, D.P., et al., "Oral administration of glutathione (GSH) increases plasma GSH concentration in humans", FASEB J.3:A1250 (5953), 1990.

Demopoulos, H.B., et al., "Free radical pathology and antioxidants in regional cerebral ischemia and central nervous system trauma", In: Anesthesia and Neurosurgery, eds. J. E. Cottrell and H. Tunndorf. C.V. Mosby, St. Louis, 1986, pp. 246–279.

Kagan, V.E., et al., "Antioxidant protection of the brain against oxidative stress", In: Free Radicals in the Brain, eds. L. Packer, L. Prilipko, and Y. Christen. Springer–Verlag, New York, 1992, Pp. 49–61.

Shan, X., et al., "Glutathione–dependent protection against oxidative injury", Pharmac. Ther. 47:61–71, 1990.

Simon, D.I., et al., "Antiplatelet properties of protein S–nitrosothiols derived from nitric oxide and endothelium–derived relaxing factor", Arterioscler. Thromb. 13(6):791–799, 1993.

Taccone–Gallucci, M., et al., "Administration of GSH has no influence on the RBC membrane: Oxidative damage . . . ", ASAIO Journal 38:855–857, 1992.

Mills, B.J., et al., "Sample processing alters glutathione and cysteine values in blood", Anal. Biochem. 184:263–267, 1990.

Richie, J.P., et al., "The determination of glutathione, cyst(e)ine, and other thiols and disulfides in biological samples using high–performance liquid chromatography with dual electrochemical detection", Anal. Biochem. 163:9–15, 1987.

Lenzi, A, et al., "Glutathione therapy for male infertility", Arch. Androl. 29:65–68, 1992.

Results of Dialog Search dated Jan. 3, 1990.

Results of Dialog Search dated Dec. 27, 1989.

Medline Abstracts Re: Guido Kroemer.

Medline Search #2.

Medline Search #3.

Medline Search #4.

Medline Search #5.

Medline Search #6.

Medline Search #7 re: Neil Kaplowitz.

Medline Search #8.

Medline Search #9 re: Keyword: Glutathione & Apoptosis.

Medline Search #10 re: Glutathione & Macular Degeneration.

Medline Search #11 re: Glutathione & Diabetes.

Medline Search #12 re: Glutathione & Restenosis.

Medline Search #13 re: Glutathione & Heart Disease.

Nakajima, T., et al., "Expression of cytochrome P450s . . . " Abstract, vol. 17: Jan.–Dec. 1996.

Dringen, Ralf, et al., "Glutathione Content as an Indicator . . . ", Journal of Neurochemistry.

May, J.M., et al., "Reduction of dehydroascorbate to ascorbate . . . ", PubMed medline query.

Bierhaus, A., et al., "Advanced glycation end product–induced activation of NF– kappaB . . . ", PubMed medline query.

Garcia De La Asuncion, Jose, et al., "Mitochondrial glutathione oxidation correlates with age–associated oxidative damage . . . ".

Willmore, W.G., et al., "Glutathione Function, Glutathion–related Enzymes and anoxia tolerance . . . ", bgw2.htm at www.carleton.ca.

Look, M.P., et al., "Serum selenium, plasma glutathione (GSH) and Erythrocyte glutathione . . . ", AIDS/HIV Selenium, GSH, GSH–Px.

Myers, C., "Information relating to HIV & Nutrition: HIV & Cysteine revisited", 7c4c22788117363a852564b400 6f598a?OpenDocument . . . .

Myers, C., "HIV/AIDS and Nutrition: Commentary re Proof–Type Studies", f67b20cedd696863852564 b8006ab698?OpenDocument . . . .

Hosein, S.R., "HIV and antioxidants", 804c6bbfcf3e 10c785256480006d406d?OpenDocument . . . .

Immunocal Milk Protein Dietary Supplement, www.myenterprises.com.

Internet Article "Key Molecule Found Critical to Surviving HIV", Doctor's Guide.

Internet Article "New Link to Alcohol–related Liver Damage Identified", Doctor's Guide.

Spielberg, S.P., et al., "Glutathione synthetase-deficient lymphocytes and acetaminophen toxicity", Medline record 81112955.

Hammarqvist, F., et al., "Skeletal muscle glutathione is depleted in critically ill patients", HealthGate Document.

Thornalley, P.J., "Negative association between erythrocyte reduced glutathione concentration and diabetic complications", HealthGate Document.

Vina, J., et al., "Exercise causes blood glutathione oxidation in chronic obstructive pulmonary disease", HealthGate Document.

Applegate, L.A., "Susceptibility of human melanoma cells to oxidative stress including UVA radiation", HealthGate Document.

Jacobasch, G., et al., "Hemolytic anemias due to erythrocyte enzyme deficiencies", HealthGate Document.

Kwasniewska, A., et al., "Frequency of HPV infection and level of glutathione in serum of women with cervix dysplasia", HealthGate Document.

Herzenberg, L.A., et al., "Glutathione deficiency is associated with impaired survival in HIV disease", HealthGate Document.

Schwartz, J.L., et al., "Glutathione inhibits experimental oral carcinogenesis, p53 expression, and angiogenesis", HealthGate Document.

Sharma, M., et al., "Hepatoprotective and toxicological evaluation of hepatomed, an ayurvedic drug", HealthGate Document.

Mohan, I.K., et al., "Oxidant stress, anti–oxidants and essential fatty acids in systemic lupus erythematosus", HealthGate Document.

Chapple, I.L., "Reactive oxygen species and antioxidants in inflammatory diseases", HealthGate Document.

Aiello, L.P., et al., "Vascular endothelial growth factor in ocular fluid of patients with diabetic retinopathy and other retinal disorders", . . . /wgetcit?journal=N+Engl+Engl+J+ Med& volume=331&page=1480&display= abstract&format=htm Oct. 22, 1999.

Baldwin, A.S., "The NF–kappa B and I kappa B proteins: new discoveries and insights", . . . /wgetcit?journal=Annu+ Rev+Immunol&volume=14&page=649&display=abstract& format=h Oct. 29, 1999.

Barcellos–Hoff, M.H., et al., "Redox–mediated activation of latent transforming growth factor–beta1", http://endo.edoc- .com/volumes/mend/vol–10.09/1077.html.

PEDF–S. Patricia Becerra, National Eye Institute Laboratory of Retinal Cell and Molecular Biology Gene Regulation, http:/www.nei.nig.gov/textsite/intramural/pedf.asp.

Berkman, R.A., et al., "Expression of the vascular permeability factor/vascular endothelial growth factor gene in central nervous system neoplasms", htt://wgetcit?journal= J+Clin+Invest&volume=91&page=153&display= abstract&format=htm.

Berndt, Kurt, "Effect of structure and stability on redox potential of glutaredoxins", http://broccoli.mfn.ki.se/kurt/ project.html.

Bryan, J.A., et al., "A retinal pigment epithelial cell–derived growth factor(s)", . . . /wgetcit?journal=Arch+ Ophthalmol&volume=104&page=422&display= abstract&format= htm Oct. 22, 1999.

Burns, M.S., et al., "The retinal pigment epithelium induces fenestration of endothelial cells in vivo", htt . . . /wgetcit- ?journal=Curr+Eye+Res&volume=11&page=863&dis- play= abstract&format=htm Oct. 22, 1999.

Campochiaro, P.A., et al., "Retinoic acid promotes density–dependent growth arrest in human retinal pigment epithelial cells", . . . /wgetcit?journal=Invest+Ophthalmol+ Vis+Sci &volume=&page=65&display=abstract&form Oct. 22, 1999.

Campochiaro, P.A., et al., "Platelet–derived growth factor is an autocrine growth stimulator . . . ", Journal of Cell Science, vol. 107 (9) 1994.

Campochiaro, P.A., et al., "Corneal endothelial cell matrix promotes expression of differentiated features . . . ", htt . . . /wgetcit?journal=Exp+Eye+Res&volume=57&page=539& display=abstract&format=htm Oct. 22, 1999.

Campochiaro, P.A., et al., "Retinal pigment epithelial cells produce PDGF–like proteins and secrete them into their media", htt . . . /wgetcit?journal+Exp+Eye+Res&volume =49&page=217&display=abstract&format=htm Oct. 22, 1999.

Clauss, M., et al., "Vascular permeability factor . . . ", htt . . . /wgetcit?journal=J+Exp+ Med&volume=172&page =1535&display=abstract&format=htm Oct. 22, 1999.

Duckett, Colin, "Structure And Function of the NF–kappa–B Family of Transcription Factors", http://www.euro.promega.com/pnotes/44/duckett/duckett.html.

Edelson, Edward, "Vessel–Growing pill looks promising", http://www.healthscout.com/egi–bin/WebObjects/Af.woa?ap=43&d=81394.

Ferrara, N., et al., "Expression of vascular endothelial growth . . . ", htt . . . /wgetcit? journal=J+Clin+ Invest&volume=91&page=160&display=abstract&format= htm Oct. 22, 1999.

Folkman, J., et al., "Angiogenic factors", http://w . . . /wgetcit?journal=Science&volume =235&page=442&display=abstract&format=htm Oct. 22, 1999.

Fujii, Junichi, et al., "Dysfunction of redox system by reactive oxygen species . . . ", http://www.3iwc.riken.go.jp/CONGRESS/SYMPO/SBF0206/AD0104/TIT.HTM Oct. 29, 1999.

Fujii, J., et al., "Down regulation of superoxide dismutases and glutathione . . . ", http://130.14.31.42/cgi–bin/VERSION_A/IGM–client?17673+records+1.

Gay, C.G., et al., "Heparin–binding growth factor–1 stimulation of human endothelial cells . . . ", h . . . /wgetcit?journal+J+Biol+Chem&volume=265&page=3284&display= abstract&format=htm Oct. 22, 1999.

Gitay–Goren, H., et al., "The binding of vascular endothelial growth factor . . . ", h . . . / wgetcit?journal=J+Biol+ Chem&volume=267&page=6093&display= abstract&format=htm Oct. 22, 1999.

Glaser, B.M., et al., "Retinal pigment epithelial cells release inhibitors . . . ", ht . . . /wgetcit? journal= Ophthalmology*volume=94&page=780&display= abstract&format=htm Oct. 22, 1999.

Harrison, Joseph, et al., "Retinal pigment epithelial dysfunction in human immunodeficiency virus . . . ", http://www.lippincott.com/ophthalmology/abstracts/v106n4Harrison.html Oct. 22, 1999.

Holmgren, Arne, "Redox regulation by the thioredoxin and glutaredoxin systems", http://www.3iwc.riken.go.jp/CONGRESS/SYMPO/SBF0206/AN0114/TIT.HTM Oct. 29, 1999.

Hopp, R.M., et al., "Apoptosis in the Murine rd1Retinal Degeneration is predominantly p53–Independent . . . ", http://www.molvis.org/molvis/v4/p5/ Oct. 22, 1999.

Hueber, Al., et al., "Daunomycin induced apoptosis in retinal pigment epithelial cells . . . ", http://www.dog.org/1998/e–abstract98/458.html Oct. 22, 1999.

Kociok, N., et al., "Expression of complement factor H in cultured retinal pigment epithelial cells", http://www-.dog.org/1998/e–abstract98/462.html.

Konstantinov, YM, et al., "Differential redox regulation by glutathione of translation . . . ", http://www.agron.missouri.edu/mnl/72/36konstantinov.html.

Korte, G.E., et al., "RPE destruction causes choriocapillary atrophy", . . . /wgetcit? journal=Invest+Ophthalmol+Vis+ Sci&volume=25&page=1135&display=abstract&f Oct. 22, 1999.

Kretz–Remy, C., et al., "Inhibition of I kappa B–alpha phosphorylation . . . ", htt . . . / wgetcit?journal=J+Cell+ Biol&volume=133&page=1083&display= abstract&format=htm Oct. 29, 1999.

Leof, E.B., et al., "Induction of c–sis mRNA and activity similar to platelet–derived growth factor . . . ", . . . /wgetcit-?journal=Proc+Natl+Acad+Sci+U+S+A&volume= 83&page= 2453&display=abstract& Oct. 22, 1999.

Leschey, K.H., et al., "Growth factor responsiveness of human retinal pigment epithelial cells", . . . /wgetcit?journal=Invest+Ophthalmol+Vis+Sci&volume=31&page= 839& display=abstract&fo Oct. 29, 1999.

Machemer, R., et al., "Pigment epithelium proliferation in retinal detachment", . . . w/ getcit?journal=Am+J+ Ophthalmol&volume=80&page+1&display= abstract&format=htm Oct. 22, 1999.

Majesky, M.W., et al., "PDGF ligand and receptor gene expression during repair of arterial injury", htt . . . /wgetcit-?journal=J+Cell+Biol&volume=111&page=2149&display= abstract&format=htm Oct. 22, 1999.

Mancini, M.A., et al., "Does the retinal pigment epithelium polarize the choriocapillaris?", . . . /wgetcit?journal=Invest+ Ophthalmol+Vis+Sci&volume=27&page= 336&display= abstract&fo Oct. 22, 1999.

Miller, H., et al., "The role of retinal pigment epithelium in the involution of subretinal neovascularization", . . . wgetcit-?journal=Invest+Ophthalmol+Vis+Sci&volume=27page= 1644&display=abstract&f Oct. 22, 1999.

Mudhar, Hardeep, et al., "PDGF and its receptors in the developing rodent retina and optic nerve", Development 118, 539–552.

Phillips, Johanna, et al., "Antisense inhibition of R–Cognin expression modulates differentiation of retinal neurons in vitro", http://www.molvis.org/molvis/v3/p12/10/22/99.

Pierce, G.F., et al., "Platelet–derived growth factor and transforming growth factor–beta enhance tissue repair activities by unique mechanisms", http . . . /wgetcit?journal= J+Cell+ Biol&volume=109&page= 429&display–abstract&format=htm Oct. 22, 1999.

Pierce, G.F., et al., "Therapeutic application of growth factors" "Role of platelet– derived growth factor in wound healing", . . . /wgetcit?journal=J+Cell+Biochem&volume= 45&page=319&display=abstract&format=htm Oct. 22, 1999.

Plate, K.H., et al., "Vascular endothelial growth factor is a potential tumour angiogenesis factor in human gliomas in vivo", http://www . . . /wgetcit?journal=Nature& volume= 359&page=845&display=abstract&format=htm Oct. 22, 1999.

Qin, Jun, et al., "Structural basis of thioredoxin–mediated redox–regulation", http://www.3iwc.riken.go.jp/CONGRESS/SYMPO/SBF0206/AI0109/TIT.HTM.

Ross, R., et al., "Localization of PDGF–B protein in macrophages in all phases of atherogenesis", http:// . . . wgetcit-?journal=Science&volume=248&page=1009&display= abstract&format=htm Oct. 22, 1999.

Rubin, K., et al., "Expression of platelet–derived growth factor receptors is induced on connective tissue cells during chronic synovial inflammation", . . . /wgetcit?journal=Scand+ J+Immunol&volume=27&page=285&display=abstract&format=htm Oct. 22, 1999.

Ryan, S.J., "The pathophysiology of proliferative vitreoretinopathy in its management", . . . /wgetcit?journal=Am+J+Ophthalmol&volume=100&page=188&display=abstract&format=htm Oct. 22, 1999.

Sarks, S.H., "Council Lecture. Drusen and their relationship to senile macular degeneration", . . . /wgetcit?journal=Aust+J+Ophthalmol&volume=8&page=117&display=abstract&format=htm Oct. 22, 1999.

Schweigerer, L., et al., "Basic fibroblast growth factor is synthesized in cultured retinal pigment epithelial cells", . . . /wgetcit?journal=Biochem+Biophys+Res+Commun& volume=143&page=934&display=abstr Oct. 22, 1999.

Seigel, Gail M., et al., "Inducible apoptosis–promoting activity in retinal cell– conditioned medium", http://www.molvis.org/molvis/v3/p14/ Oct. 22, 1999.

Sen, Chandan K., et al., "Therapeutic potential of a–Lipoic acid: molecular aspects", http://www.3iwc.riken.go.jp/CONGRESS/SYMPO/SBF0206/AE0105/TIT.HTM.

Sen, Chandan K., et al., "Cellular thiol redox status", http://packer.berkeley.edu/ research/Cell/thiol Oct. 29, 1999.

Stramm, L., et al., "Disease expression in cultured pigment epithelium. Feline mucopolysaccharidosis VI", . . . /wgetcit?journal=Invest+Ophthalmol+Vis+Sci&volume=26&page=182&display=abstract&fo Oct. 22, 1999.

Vlodavsky, I., et al., "Aortic endothelial cells synthesize basic fibroblast growth factor . . . ", . . . /wgetcit?journal=J+Cell+Physiol&volume=131&page=402&display=abstract& format=htm Oct. 22, 1999.

Wong, H.C., et al., "Retinal pigment epithelial cells in culture produce retinal vascular mitogents", . . . /wgetcit?journal=Arch+Ophthalmol&volume=106&page=1439&display= abstract&format=htm Oct. 22, 1999.

Yang, Q.R., et al., "Human retinal pigment epithelial cells from different donors continuously produce a vascular endothelial cell–stimulating factor into serum–free medium" http://usa.biologists.com/JCS/104/01/jcs7729f.html. Oct. 22, 1999.

Young, R.W., "Pathophysiology of age–related macular degeneration", . . . w/wgetcit? journal=Surv+Ophthalmol&volume=31&page=291&display=abstract&format=htm Oct. 22, 1999.

Fabi, Randy, "Artificially grown sex organs–may soon be possible", http: . . . /story?StoryId=CocUE0b8ZtJeYmZCWmdu&FQ=apomorphine&Nav=na–search–&StoryTitle= apomorphin Nov. 19, 1999.

Internet Article "Apomorphine: The rediscovery of an Old Treatment for Parkinson's Desease?", http://www.newsalert.com/bi . . . :7RWbWbtu5nmdal&FQ=apomorphine&Nav=na–search–&StoryTitle=apomorphin Nov. 19, 1999.

Internet Article "Apomorphine SL Study Mar. 1, 1994", http://urology.columbia.edu/ sexualdysfunc/apomorphine/sld006.htm Nov. 19, 1999.

Internet Article "Apomorphine, Sildensafil and Phentolamine", http://63.72.98.30/content/ article.asp?articleid=25.

Firfer, Holly, "Study finds new therapy for impotence", Oct. 27, 1999, http://cnn.com. /HEALTH/men/9910/27/erection.drug/index.html Oct. 28, 1999.

Crayhon, Robert, "The real power of antioxidants", http://ehostvgw3.epnet.com/ print2.asp?re . . . r=&hitNum=2&cacheControl=loaded&x=41&y=9.

Frank, Robert, et al., "Antioxidant enzymes in the macular retinal pigment epithelium of eyes with neovascular age–related macular degeneration".

Kowluru, Renu, et al., Effects of antioxidants (Abnormalities of retinal metabolism in diabetes or experimental galactosemia, part 3).

"Nutrients combat macular degeneration" (excerpted from the Journal of the American Medical Association, Nov. 8, 1994).

Christen, William, "Antioxidants and eye disease. (Health Promotion and Disease Preventive: The Role of Antioxidant Vitamins)", American Journal of Medicine, Sep. 26, 1994, v97, n3A p14S(4).

Friberg, Thomas, Age–related macular degeneration (Review) title page.

Starr, Christopher, et al., "Age–related macular degeneration: can we stem this worldwide public health crisis?", Postgraduate Medicine, May 1998 v103 n5 p153(9).

"Combating a common blindness (drug visudyne may help treat macular degeneration)" (Brief Article) copyright 1999 Maclean Hunter (Canada).

Adler, Tina, "Beta–carotene may lower vitamin E stores" (Brief Article) copyright 1994 Science Service Inc.

Mahi, Josephine, "Macular degeneration and lutein", Total Health, Mar.–Apr. 1997 v19n1 p21(1).

"OTC vitamin products to prevent cataracts and macular degeneration", copyright 1995 Center for Medical Consumers Inc.

"Antioxidants may deter macular degeneration", copyright 1994 Argus Press.

Hershman, Tania, "Flaccid Flowers Bloom on Viagra", Wired News, Aug. 9, 1999.

"Industry/University Group Finds HDL Regulatory Gene", Genetic Engineering News. vol. 19, No. 15, Sep. 1, 1999.

"Australians Target Prostate Cancer and BPH", Genetic Engineering News, Sep. 1, 1999.

Cover sheet "Antioxidants & Redox Signaling", vol. 1 No. 1, Spring 1999.

Glaser, Vicki, "AtheroGenics attacks plaque", Genetic Engineering News, Sep. 1, 1999.

Fox, Sophia, "Bayer Funds Collaboration", Genetic Engineering News, Sep. 1, 1999.

Wu, YQ, et al., "Proteolytic activity directed toward pigment epithelium–derived factor . . . ", http://130.14.32.44/cgi–bin/VERSION_B/IGM–client?8314+records+1 Aug. 4, 1999.

Marcus, Adam, "Antioxidants may prevent pregnancy problem", http://www. healthscout.com/cgi–bin/WebObjects/Af.woa?ap=43&id=65283 Sep. 8, 1999.

"Antioxidants may fight rare killer disease", http://cnn.com/HEALTH/9908/16/rare.disease. ap/index.html Aug. 17, 1999.

National Library of Medicine: IGM Details of Search Screen, http://130.14.32.44/cgi–bin/VERSION_ B/IGM–client?8314+records+21.

* cited by examiner

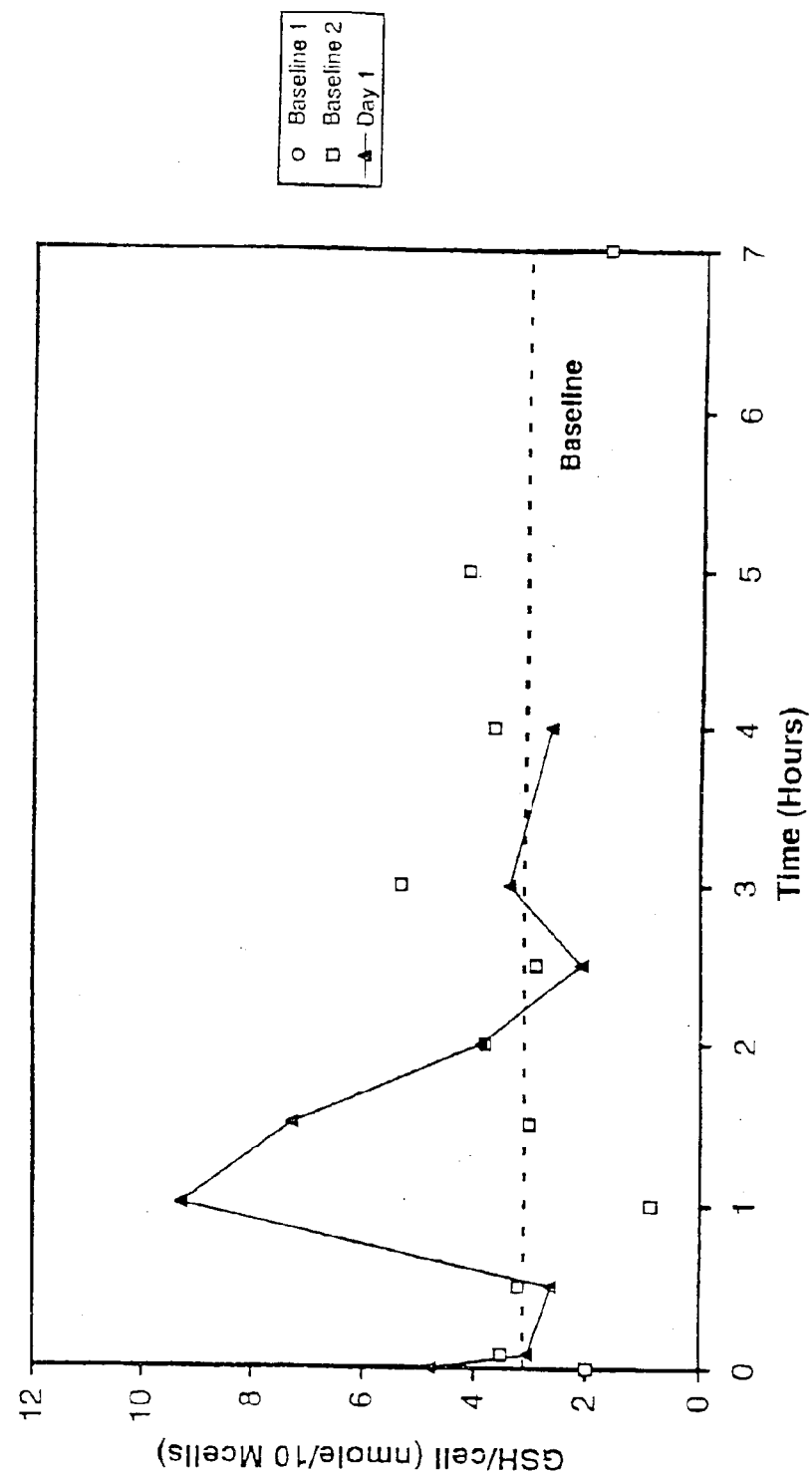

Thyone™-500, Given Orally, Markedly Raises Glutathione Levels Inside the Immune Cells of HIV Positive People.

| Dosage Regimen | Responders | Percent Increases |
| --- | --- | --- |
| 3 grams/day<br>1.5 Grams, 2x/day | 100%<br>6 out of 6 people<br>Average Ranges: | 53% - 99% |
| 2 grams/day<br>1.0 grams, 2x/day | 75%<br>6 out of 8 people<br>Average Ranges: | 42% - 87% |
| 1 gram/day<br>0.5 grams, 2x/day | 40%<br>2 out of 5 people<br>Average Ranges: | 8% - 60% |

These results show a dose-response effect in that 3 grams/day result in positive responses, in more people, and the responses are greater...compared to 2 grams/day, and 1 gram/day.

Fig. 2

PHARMACEUTICAL PREPARATIONS OF GLUTATHIONE AND METHODS OF ADMINISTRATION THEREOF

The present application claims benefit of priority from Provisional Patent Application No. 60/034,101, filed Dec. 31, 1996, and claims benefit of priority under 35 U.S.C. § 371 from PCT/US97/23879, filed Dec. 31, 1997, and is a continuation of U.S. patent application Ser. No. 09/331,947, filed Jun. 28, 1999, to be issued as U.S. Pat. No. 6,350,467 on Feb. 26, 2002, each of which is expressly incorporated herein by reference. This application is related to U.S. patent application Ser. No. 09/002,100, now U.S. Pat. No. 6,159,500, U.S. patent application Ser. No. 09/457,642, now U.S. Pat. No. 6,204,248, and U.S. patent application Ser. No. 09/813,247 U.S. Pat. No. 6,423,687 B1 (allowed).

FIELD OF THE INVENTION

The present invention relates to the field of antioxidant administration to mammals, and more particularly to the field of glutathione therapies as sole and combination therapies for mammals in need of such treatment.

BACKGROUND OF THE INVENTION

The ubiquitous tripeptide L-glutathione (GSH) (gamma-glutamyl-cysteinyl-glycine), is a well known biological antioxidant, and in fact is believed to be the primary intracellular antioxidant for higher organisms. When oxidized, it forms a dimer (GSSG), which may be recycled in organs having glutathione reductase. Glutathione may be transported through membranes by the sodium-dependent glutamate pump. Tanuguchi, N., et al. Eds., *Glutathione Centennial*, Academic Press, New York (1989), expressly incorporated herein by reference.

GSH is known to function directly or indirectly in many important biological phenomena, including the synthesis of proteins and DNA, transport, enzyme activity, metabolism, and protection of cells from free-radical mediated damage. GSH is one of the primary cellular antioxidants responsible for maintaining the proper oxidation state within the body. GSH is synthesized by most cells, and is also supplied in the diet. GSH has been shown to recycle oxidized biomolecules back to their active, reduced forms.

Reduced glutathione (GSH) is, in the human adult, produced from oxidized glutathione (GSSG) primarily by the liver, and to a smaller extent, by the skeletal muscle, red blood cells, and white cells. About 80% of the 8–10 grams glutathione produced daily is produced by the liver and distributed through the blood stream to the other tissues.

A deficiency of glutathione in cells may lead to excess free radicals, which cause macromolecular breakdown, lipid peroxidation, buildup of toxins, and ultimately cell death. Because of the importance of glutathione in preventing this cellular oxidation, glutathione is continuously supplied to the tissues. However, under certain conditions, the normal, physiologic supplies of glutathione are insufficient, distribution inadequate or local oxidative demands too high to prevent cellular oxidation. Under certain conditions, the production of and demand for glutathione are mismatched, leading to insufficient levels on an organismal level. In other cases, certain tissues or biological processes consume glutathione so that the intracellular levels are suppressed. In either case, by increasing the serum levels of glutathione, increased amounts may be directed into the cells. In facilitated transport systems for cellular uptake, the concentration gradient which drives uptake is increased.

As with all nutrients, it would normally be considered to eat or orally ingest the nutrient to increase body levels. Thus, attempts at oral glutathione treatments were known, and indeed the present inventors hereof previously suggested oral glutathione administration for various indications. The protocols for administration of glutathione, however, were not optimized and therefore the bioavailability of the glutathione was unassured and variable. All prior pharmaceutical attempts by others to safely, effectively and predictably raise intracellular GSH through oral therapy with GSH have not met with demonstrated success. Experts generally believe that beneficial physiological effects of orally administered glutathione are difficult or impossible to achieve, or the efficiency is so low as to make supplementation by this route unproductive.

Because of the poor or variable results obtained, the art generally teaches that oral administration of glutathione is ineffective, forcing administration or supplementation by other routes, principally intravenously, but also by alveolar inhalation. Orally absorbed prodrugs and precursors have also been proposed or used. A known pharmacological regimen provides intravenous glutathione in combination with another agent, such as cis-platinum (a free radical associated metal drug), doxorubicin, or daunorubicin (free radical associated drugs which interact with nucleic acid metabolism), which produced toxic side effects related to free radical reactions.

The ability to harness GSH, which is a powerful, but safe substance, into an effective oral pharmaceutical had not been accomplished in the past, because of molecular instability, poor gastrointestinal absorption through existing protocols and resulting inability to reliably effect increases in intracellular GSH levels. Administering sufficient amounts to achieve physiological benefit using known oral administration protocols might lead to cysteine related kidney stones, gastric distress or flatulence.

Glutathione is relatively unstable in alkaline or oxidative environments, and is not absorbed by the stomach. It is believed that glutathione is absorbed, after oral administration, if at all, in the latter half of the duodenum and the beginning of the jejunum. It was also believed that orally administered glutathione would tend to be degraded in the stomach, and that it is particularly degraded under alkaline conditions by desulfurases and peptidases present in the duodenum. Thus, known protocols for oral administration of glutathione involved administered with meals or after eating to buffer pH extremes and dilute degradative enzymes. This protocol, however, has the effect of diluting the glutathione and delaying absorption. Studies directed at determining the oral bioavailability of glutathione under such circumstances showed poor absorption, and therefore such administration was seen as of little benefit.

Therefore, while oral dosage forms of glutathione were known, the clinical benefits of these formulations were unproved and, given the lack of predictability of their effect, these formulations were not used for the treatment of specific conditions, nor proven to have effect. Further, the known protocols for administration of glutathione did not provide convenience and high bioavailability.

The prior art thus suggests that glutathione esters might be suitable as orally bioavailable sources of glutathione, which are stable and may be rapidly absorbed. However, these are both more expensive than glutathione itself and have proven toxic.

Pure glutathione forms a flaky powder which retains a static electrical charge, due to triboelectric effects, that makes processing difficult. The powder may also have an electrostatic polarization, which is akin to an electret. Glutathione is a strong reducing agent, so that autooxidation occurs in the presence of oxygen or other oxidizing agents. U.S. Pat. No. 5,204,114, Demopoulos et al., expressly incorporated herein by reference in its entirety, provides a method of manufacturing glutathione tablets and capsules by the use of crystalline ascorbic acid as an additive to reduce triboelectric effects which interfere with high speed equipment and maintaining glutathione in a reduced state. A certain crystalline ascorbic acid is, in turn, disclosed in U.S. Pat. No. 4,454,125, Demopoulos, expressly incorporated by reference herein in its entirety. This crystalline form is useful as a lubricating agent for machinery. Ascorbic acid has the advantage that it is well tolerated, antioxidant, and reduces the net static charge on the glutathione.

In synthesizing glutathione in the body, cysteine, a thiol amino acid is required. Since the prior art suggests that oral administration of glutathione itself would be ineffective, prodrugs or precursor therapy was advocated. Therefore, the prior art suggests administration of cysteine, or a more bioavailable precursor of cysteine, N-acetyl cysteine (NAC). While cysteine and NAC are both, themselves, antioxidants, their presence competes with glutathione for resources in certain reducing (GSH recycling) pathways. Since glutathione is a specific substrate for many reducing pathways, the loading of a host with cysteine or NAC may result in less efficient utilization or recycling of glutathione. Thus, cysteine and NAC are not ideal GSH prodrugs. Thus, while GSH may be degraded, transported as amino acids, and resynthesized in the cell, there may also be circumstances where GSH is transported into cells without degradation; and in fact the administration of cysteine or cysteine precursors may interfere with this process.

A number of disease states have been specifically associated with reductions in glutathione levels. Depressed glutathione levels, either locally in particular organs, or systemically, have been associated with a number of clinically defined diseases and disease states. These include HIV/AIDS, diabetes and macular degeneration, all of which progress because of excessive free radical reactions and insufficient GSH. Other chronic conditions may also be associated with GSH deficiency, including heart failure and coronary artery restenosis post angioplasty.

For example, diabetes afflicts 8% of the United States population and consumes nearly 15% of all United States healthcare costs. HIV/AIDS has infected nearly 1 million Americans. Current therapies cost in excess of $20,000 per year per patient, and are rejected by, or fail in 25% to 40% of all patients. Macular degeneration presently is considered incurable, and will afflict 15 million Americans by 2002.

Clinical and pre-clinical studies have demonstrated the linkage between a range of free radical disorders and insufficient GSH levels. Newly published data implies that diabetic complications are the result of hyperglycemic episodes that promote glycation of cellular enzymes and thereby inactivate GSH synthetic pathways. The result is GSH deficiency in diabetics, which may explain the prevalence of cataracts, hypertension, occlusive atherosclerosis, and susceptibility to infections in these patients.

GSH functions as a detoxicant by forming GSH S-conjugates with carcinogenic electrophilcs, preventing reaction with DNA, and chelation complexes with heavy metals such as nickel, lead, cadmium, mercury, vanadium, and manganese. GSH also plays a role in metabolism of various drugs, such as opiates. It has been used as an adjunct therapy to treatment with nephrotoxic chemotherapeutic agents such as cisplatin, and has been reported to prevent doxorubicin-induced cardiomyopathy. GSH is also an important factor in the detoxification of acetaminophen and ethanol, two powerful hepatotoxins.

(I) HIV

High GSH levels have been demonstrated to be necessary for proper functioning of platelets, vascular endothelial cells, macrophages, cytotoxic T-lymphocytes, and other immune system components. Recently it has been discovered that HIV-infected patients exhibit low GSH levels in plasma, in other fluids, and in certain cell types like macrophages, which does not appear to be due to defects in GSH synthesis. GSH has been shown to inhibit HIV replication in chronically-infected cells and in cells acutely infected in vitro. This makes GSH replacement therapy attractive, because it has the potential to interfere with the expression of the integrated HIV genome, a site that is not attacked by the currently employed antiretrovirals (AZT, ddI, ddC, D4T). GSH may also have benefits in countering the excess free radical reactions in HIV infection, which may be attributable to: 1) the hypersecretion of TNF-$\alpha$ by B-lymphocytes, in HIV infection, and 2) the catalysis of arachidonic acid metabolism by the gp 120 protein of HIV. The physiologic requirements for GSH by key cell types of the immune system, and the ability of macrophages to take up intercellular GSH, as well as to metabolically interact with T-lymphocytes to indirectly cause their GSH to increase, offer additional reasons to attempt to correct the GSH deficiency in HIV/AIDS.

In other new data dealing with HIV infections, the March 1997 issue of the Proceedings of the National Academy of Sciences (PNAS) established ". . . GSH deficiency as a key determinant of survival in HIV disease . . . " GSH deficiency is associated with impaired survival in HIV disease (PNAS. Vol. 94, pp. 1967–1972). The quest to raise GSH levels in cells is widely recognized as being extremely important in HIV/AIDS and other disorders, because the low cellular GSH levels in these disease processes permit more and more free radical reactions to propel the disorders.

HIV is known to start pathologic free radical reactions which lead to the destruction of GSH, as well as exhaustion of other antioxidant systems and destruction of cellular organelles and macromolecules. In pre-clinical studies, GSH stops the replication of the virus at a unique point, and specifically prevents the production of toxic free radicals, prostaglandins, TNF-$\alpha$, interleukins, and a spectrum of oxidized lipids and proteins that are immunosuppressive, cause muscle wasting and neurologic symptoms. Restoring GSH levels could slow or stop the diseases progression, safely and economically.

In mammalian cells, oxidative stresses, i.e., low intracellular levels of reduced GSH, and relatively high levels of free radicals, activate certain cytokines, including NF$\kappa$B and TNF-$\alpha$, which, in turn, activate cellular transcription of the DNA to mRNA, resulting in translation of the mRNA to a polypeptide sequence. In a virus infected cell, the viral genome is transcribed, resulting in viral RNA production, generally necessary for viral replication of RNA viruses and retroviruses. These processes require a relatively oxidized state of the cell, a condition which results from stress, low glutathione levels, or the production of reduced cellular products. The mechanism which activates cellular transcription is evolutionarily highly conserved, and therefore it is unlikely that a set of mutations would escape this process, or that an organism in which mutated enzyme and receptor gene products in this pathway would be well adapted for survival. Thus, by maintaining a relatively reduced state of the cell (redox potential), viral transcription, a necessary step in late stage viral replication, is impeded.

The amplification effect of oxidative intracellular conditions on viral replication is compounded by the actions of various viruses and viral products which degrade GSH. For example, GP-120, an HIV surface glycoprotein having a large number of disulfide bonds, and normally present on the surface of infected cells, oxidizes GSH, resulting in reduced intracellular GSH levels. On the other hand, GSH reduces disulfide bonds of GP-120, reducing or eliminating its biological activity, necessary for viral infectivity. GSH therefore interferes with the production of such oxidized proteins, and degrades them once formed. In a cell which is actively replicating viral gene products, a cascade of events may occur which allow the cell to pass from a relatively quiescent stage with low viral activity to an active stage with massive viral replication and cell death, accompanied by a change in redox potential; by maintaining adequate GSH levels, this cascade may be impeded.

Thus, certain viral infections, such as HIV, are associated with reduced GSH levels, and it is believed that by increasing intracellular GSH levels in infected cells, as well as increasing extracellular GSH, the replication of HIV may be interfered with, and the cascade of events delayed or halted. It is noted that AIDS may also be associated with reduced GSSG levels, implying an interference with de novo synthesis of GSH as well as the oxidation of existing GSH discussed above.

The Human Immunodeficiency Virus (HIV) is transmitted through two predominant routes, contaminated blood and/or sexual intercourse. In pediatric cases, approximately one half are infected in utero, and one half at delivery. This circumstance permits a study of prevention of transmission since the time of spread is known. Initially, there is an intense viral infection simulating a severe case of the flu, with massive replication of the virus. This acute phase passes within weeks, spontaneously, as the body mounts a largely successful immune defense. Thereafter, the individual has no outward manifestations of the infection. However, the virus continues to replicate, insidiously, within immune system tissues and cells, like lymph nodes, lymphoid nodules and special multidendritic cells that are found in various body cavities.

This infection is not just a viral problem. The virus, in addition to replicating, causes excessive production of various free radicals and various cytokines in toxic or elevated levels. The latter are normally occurring biochemical substances that signal numerous reactions, usually exist in minuscule concentrations. Eventually, after an average of 7–10 years, of seemingly quiescent HIV infection, the corrosive free radicals and the toxic levels of cytokines begin to cause symptoms, and failures in the immune system begin. Substances like 15-HPETE are immunosuppressive and TNF-$\alpha$ causes muscle wasting, among other toxic factors. The numbers of viral particles increase and the patient develops the Acquired Immune Deficiency Syndrome, AIDS, which may last 2 to 4 years before the individual's demise. AIDS, therefore, is not simply a virus infection, although the viral infection is believed to be an integral part of the etiology of the disease.

HIV has a powerful ability to mutate. It is this capability that makes it difficult to create a vaccine or to develop long-term anti-viral pharmaceutical treatments. As more people continue to fail the present complex regimens, the number of resistant viral strains is increasing. This is a particularly dangerous pool of HIV and poses a considerable threat. These resistant mutants also add to the difficulties in developing vaccines. This epidemic infection is out of control, and the widely popularized polypharmaceutical regimens that are aimed only at lowering the number of viruses are proving to be too complex, too toxic, too costly, and too narrow. As a result, in the past 1.5 years since the introduction of protease inhibitors, in combination with AZT-type drugs, increasing numbers of people are failing therapy, approximately 25% and growing. Further, the continuing production of free radicals and cytokines that may become largely independent of the virus, perpetuate the dysfunctions of the immune system, the gastrointestinal tract, the nervous system, and many other organs in AIDS. The published scientific literature indicates that many of these diverse organ system dysfunctions are due to systemic GSH deficiencies that are engendered by the virus and its free radicals. GSH is consumed in HIV infections because it is the principal, bulwark antioxidant versus free radicals. An additional cause of erosion of GSH levels is the presence of numerous disulfide bonds (—S—S—) in HIV proteins, such as the GP-120 discussed above. Disulfide bonds react with GSH and oxidize it.

This disease obviously is not controllable with the present approaches and basically can not be curtailed in its spread merely by superficial public health messages regarding safe sex and clean needles, or by using overly complex, toxic, costly medications that are narrowly aimed at just viral replication.

The current HIV/AIDS pharmaceuticals take good advantage of the concept of pharmaceutical synergism, wherein two different targets in one process are hit simultaneously. The effect is more than additive. The drugs now in use were selected to inhibit two very different points in the long path of viral replication. The pathway of viral replication can be depicted simply:

HIV Replication Pathway

| ------→ | ------→ | ------→ | ------→ | ------→ |
|---------|---------|---------|---------|---------|
| point #1 | point #2 | point #3 | point #4 | point #5 |
| Virus attacks and enters the cell | Virus makes DNA from its RNA | Viral DNA is integrated into cells' DNA | Proviral DNA is inactive for a long time, but activators will start HIV replicating rapidly | Viral RNA is produced, along with viral membranes and proteins, which are assembled |

-continued

HIV Replication Pathway

| point #1 → | point #2 → | point #3 → | point #4 → | point #5 → |
|---|---|---|---|---|
| Viral gp120 protein and CD4+ cell receptors and others are involved | Reverse transcriptase is the enzyme involved | Integrase is the enzyme involved | NF kappa B is the activator of dormant HIV DNA and glutathione levels must be low for activation to occur | Viral protease is involved |
|  | AZT, ddI, ddC |  | Glutathione | Protease Inhibitors |

Point #2 was the earliest point of attack, using AZT-types of drugs, including ddI, ddC and others. These are toxic and eventually viruses become resistant to these Reverse Transcriptase inhibitors.

Point #5 is a late replication step, and this is where protease inhibitors function. The drug blocks viral protease, an enzyme that snips long protein chains to just the right length so the viral coat fits exactly around the nucleic acid core, and that proteins having different biological activities are separated. By themselves, protease inhibitors foster the rapid development of resistant, mutant strains.

By combining Reverse Transcriptase inhibitors plus protease inhibitors, synergism was obtained and the amounts of viral particles in the plasma plummeted, while the speed of the developing mutant resistant viral strains was slowed, compared to using only one type of inhibitor. This combination has been in use for about 1.5 years, and so far, about 25% to 40% of U.S. patients have failed the treatment. This number is expected to rise as resistant mutants develop, albeit more slowly than the use of the drugs separately.

In addition to the multiple drugs aimed at the virus, at points #2 and #5, AIDS patients and progressing HIV positive people who have not yet developed an AIDS-related disease, also take other pharmaceuticals, the most common being one to prevent the unusual pneumonia caused by Pneumocystis carinii, for example trimethoprim-sulfathiazole. As other opportunistic infections occur with fungi, yeasts, bacteria, tuberculosis, and other viruses like cytomegalovirus infection of the retinae, the number of pharmaceuticals increases greatly. Sadly, AIDS patients are also more likely to develop cancers, such as lymphomas, cancer of the cervix and Kaposi's sarcoma. Management of the cancers requires the addition of still more drugs.

New therapies include additional drugs in the classes of Reverse Transcriptase inhibitors and protease inhibitors. Also, drugs are in development to block point #3, wherein the enzyme, integrase, integrates the HIV DNA into the infected cell's DNA, analogous to splicing a small length of wire into a longer wire. Vaccine development also continues, although prospects seem poor because HIV appears to be a moving target and seems to change as rapidly as a chameleon. Vaccine development is also impaired by the immune cell affinity of the virus.

Human Immunodeficiency virus-infected individuals have lowered levels of serum acid-soluble thiols and GSH in plasma, peripheral blood monocytes, and lung epithelial lining fluid. In addition, it has been shown that CD4+ and CD8+ T cells with high intracellular GSH levels are selectively lost as HIV infection progresses. This deficiency may potentiate HIV replication and accelerate disease progression, especially in individuals with increased concentrations of inflammatory cytokines because such cytokines stimulate HIV replication more efficiently in GSH-depleted cells. GSH and glutathione precursors such as N-acetyl cysteine (NAC) can inhibit cytokine-stimulated HIV expression and replication in acutely infected cells, chronically infected cells, and in normal peripheral blood mononuclear cells.

It is noted that depletion of GSH is also associated with a processes known as apoptosis, or programmed cell death. Thus, intercellular processes which artificially deplete GSH may lead to cell death, even if the process itself is not lethal.

2) Diabetes Mellitus

Diabetes mellitus is found in two forms, childhood or autoimmune (type I, IDDM) and late-onset or non-insulin dependent (type II, NIDDM). The former constitute about 30% and the remainder represent the bulk of cases seen. Onset is generally sudden for Type I, and insidious for Type II. Symptoms include excessive urination, hunger and thirst with a slow steady loss of weight in the first form. Obesity is often associated with the second form and has been thought to be a causal factor in susceptible individuals. Blood sugar is often high and there is frequent spilling of sugar in the urine. If the condition goes untreated, the victim may develop ketoacidosis with a foul-smelling breath similar to someone who has been drinking alcohol. The immediate medical complications of untreated diabetes can include nervous system symptoms, and even diabetic coma.

Because of the continuous and pernicious occurrence of hyperglucosemia (very high blood sugar levels), a non-enzymatic chemical reaction occurs called glycation. Since glycation occurs far more frequently inside cells, the inactivation of essential enzyme proteins happens almost continually. One of the most critical enzymes, γ-glutamyl-cysteine synthetase, is glycated and readily inactivated. This enzyme is the crucial step in the biosynthesis of glutathione in the liver.

The net result of this particular glycation is a deficiency in the production of GSH in diabetics. Normally, adults produce 8–10 grams every 24 hours, and it is rapidly oxidized by the cells. GSH is in high demand throughout the body for multiple, essential functions, for example, within all mitochondria, to produce chemical energy called ATP. Brain cells, heart cells, and others simply will not function well and can be destroyed through apoptosis.

GSH is the major antioxidant in the human body and the only one we are able to synthesize, de novo. It is also the most common small molecular weight thiol in both plants and animals. Without GSH the immune system cannot function, and the central and peripheral nervous systems become aberrant and then cease to function. Because of the dependence on GSH as the carrier of nitric oxide, a vasodilator responsible for control of vascular tone, the cardiovascular system does not function well and eventually fails. Since all epithelial cells seem to require GSH, the intestinal lining cells don't function properly and valuable micronutrients are lost, nutrition is compromised, and microbes are given portals of entry to cause infections.

The use of GSH precursors cannot help to control the GSH deficiency due to the destruction of the rate-limiting enzyme by glycation. As GSH deficiency becomes more profound, the well-known sequellae of diabetes progress in severity. The complications described below are essentially due to runaway free radical damage since the available GSH supplies in diabetics are insufficient.

The diabetic will become more susceptible to infections because the immune system approaches collapse when GSH levels fall . . . analogous to HIV/AIDS. Peripheral vasculature becomes compromised and blood supply to the extremities is severely diminished because GSH is not available in sufficient amounts to stabilize the nitric oxide (•NO) to effectively exert its vascular dilation (relaxation) property. Gangrene is a common sequel and successive amputations are often the result in later years.

Peripheral neuropathies, the loss of sensation commonly of the feet and lower extremities develop, often followed by aberrant sensations like burning or itching which can't be controlled. Retinopathy and nephropathy are later events which are actually due to microangiopathy, excessive budding and growth of new blood vessels and capillaries, which often will bleed due to weakness of the new vessel walls. This bleeding causes damage to the retina and kidneys with resulting blindness and renal shutdown, the latter results in required dialysis. Cataracts occur with increasing frequency as the GSH deficiency deepens.

Large and medium sized arteries become sites of accelerated, severe atherosclerosis, with myocardial infarcts at early ages, and of a more severe degree. If diabetics go into heart failure, their mortality rates at one year later are far greater than in non-diabetics. Further, if coronary angioplasty is used to treat their severe atherosclerosis, diabetics are much more likely to have renarrowing of cardiac vessels, termed restenosis.

The above complications are due, in large measure, to GSH deficiency and ongoing free radical reactions. These sequellae frequently and eventually occur despite the use of insulin injections daily that lower blood sugar levels. Good control of blood sugar levels is difficult for the majority of diabetics.

3) Macular Degeneration

Approximately 1 million people in the United States have significant macular degeneration. One out of every 4 persons aged 55 or above now has macular degeneration and 1 in 2 above the age of 80. As our population ages this principal cause of blindness in the elderly will increase as well. By the year 2002, 15 million people in the U.S. will suffer from macular degeneration.

Age-related macular degeneration (ARMD) is the disease characterized by either a slow (dry form) or rapid (wet form) onset of destruction and irrevocable loss of rods and cones in the macula of the eye. The macula is the approximate center of the retina wherein the lens of the eye focuses its most intense light. The visual cells, known as the rods and cones, are an outgrowth and active part of the central nervous system. They are responsible and essential for the fine visual discrimination required to see clear details such as faces and facial expression, reading, driving, operation of machinery and electrical equipment and general recognition of surroundings. Ultimately, the destruction of the rods and cones leads to functional, legal blindness. Since there is no overt pain associated with the condition, the first warnings of onset are usually noticeable loss of visual acuity. This may already signal late stage events. It is now thought that one of the very first events in this pathologic process is the formation of a material called "drusen".

Drusen first appears as either patches or diffuse drops of yellow material deposited upon the surface of the retina in the macula lutea or yellow spot. This is the area of the retina where sunlight is focused by the lens. It is the area of the retina which contains the highest density of rods for acuity. Although cones, which detect color are lost as well in this disease, it is believed to be loss of rods which causes the blindness. Drusen has been chemically analyzed and found to be composed of a mixture of lipids much of it peroxidized by free radical reactions. The Drusen first appears as small collections of material at the base of Bruch's membrane. This produces "bubbles" which push the first layer of cells up off the membrane. Vascular budding, neovascular growth, first appears in these channels. This first layer of cells is unique.

They are retinal pigmented epithelial (RPE) cells and these cells are distantly related to CNS microglia and have a phagocytic function. They are also the layer of cells immediately below the primary retinal cells, the rods and cones. The RPE cells are believed to serve a protective function for the rods and cones since they consume the debris cast off by the rods and cones. It is not known yet whether the pigmented material serves a protective function or is related to phagocytosis only. However, this pigment although concentrated in organelles, is believed to be composed of peroxidized lipids and melanin.

It is believed, because of the order of events in model systems, that the loss of RPE cells occurs first in ARMD (Age Related Macular Degeneration). Once an area of the retinal macula is devoid of RPE cells, loss of rods, and eventually some cones, occurs. Finally, budding of capillaries begins and we see the typical microangiopathy associated with late stage ARMD. It is also known that RPE cells require large quantities of GSH for their proper functioning. When GSH levels drop severely in these cells, in cell cultures where they can be studied, these cells begin to die. When cultures of these cells are supplemented with GSH in the medium, they thrive. There is increasing evidence that progression of the disease is paced by a more profound deficiency in GSH within the retina and probably within these cells, as indicated by cell culture studies.

It is generally believed that "near" ultraviolet (UVB) and visual light of high intensity primarily from sunlight is a strong contributing factor of ARMD. People with light-colored irises constitute a population at high risk, as do those with jobs which leave them outdoors and in equatorial areas where sunlight is most intense. Additional free radical insults, like smoking, adds to the risk of developing ARMD.

Several approaches have been recently tested, including chemotherapy, without success. Currently, there is no effective therapy to treat ARMD. Laser therapy has been developed which has been used widely to slow the damage produced in the slow onset form of the disease by cauterizing neovascular growth. However the eventual outcome of the disease, once it has started to progress, is certain.

Metabolism of Glutathione

The synthesis of GSH is dependent upon the availability of cysteine either supplied directly from the diet or cysteine or indirectly from methionine via the transsulfuration pathway. GSH synthesis and metabolism is governed by the enzymes of the γ-glutamyl cycle as shown in FIG. 1. GSH is synthesized intracellularly by the consecutive actions of γ-glutamylcysteinyl synthetase (Reaction 1) and GSH synthetase (Reaction 2). The action of the latter enzyme is feedback inhibited by GSH. The breakdown of GSH (and also of its oxidized form, GSSG) is catalyzed by γ-glutamyl transpeptidase, which catalyzes the transfer of the gamma-glutamyl moiety to acceptors such as sulfhydryl-containing amino acids, certain dipeptides, and GSH itself (Reaction 3). The cellular turnover of GSH is associated with its transport, in the form of GSH, across cell membranes, where the majority of the transpeptidase is found. During this transport, GSH interacts with γ-glutamyl transferase (also known as transpeptidase) to form γ-glutamyl amino acids which are transported into cells. Intracellular γ-glutamyl amino acids are substrates of γ-glutamyl cyclotransferase (Reaction 4) which converts these compounds into the corresponding amino acids and 5-oxo-L-proline. The ATP-dependent conversion of 5-L-oxoproline to L-glutamate is catalyzed by the intracellular enzyme 5-oxo-prolinase (Reaction 5). The cysteinylglycine formed in the transpeptidase reaction is split by dipeptidase (Reaction 6). These six reactions constitute the γ-glutamyl cycle, which accounts for the synthesis and enzymatic degradation of GSH.

Two of the enzymes of the cycle also function in the metabolism of S-substituted GSH derivatives, which may be formed nonenzymatically by reaction of GSH with certain electrophilic compounds or by GSH S-transferases (Reaction 7). The γ-glutamyl moiety of such conjugates is removed by the action of γ-glutamyl transpeptidase (Reaction 3), a reaction facilitated by γ-glutamyl amino acid formation. The resulting S-substituted cysteinylglycines are cleaved by dipeptidase (Reaction 6A) to yield the corresponding S-substituted cysteines, which may undergo N-acetylation (Reaction 8) or an additional transpeptidation reaction to form the corresponding γ-glutamyl derivative (Reaction 3A).

Intracellular GSH is converted to its oxidized, dimeric form (GSSG) by selenium-containing GSH peroxidase, which catalyzes the reduction of $H_2O_2$ and other peroxides (Reaction 9). GSH is also converted to GSSG by transhydrogenation (Reaction 10). Reduction of GSSG to GSH is mediated by the widely-distributed enzyme GSSG reductase which uses NADPH (Reaction 11). Extracellular conversion of GSH to GSSG has also been reported; the overall reaction requires $O_2$ and leads to the formation of $H_2O_2$ (Reaction 12). GSSG is also formed by reaction of GSH with free radicals.

Transport of Glutathione

The intracellular level of GSH in mammalian cells is in the range of 0.5–10 millimolar, while micromolar concentrations are typically found in blood plasma. Intracellular glutathione is normally over 99% reduced form (GSH). The normal healthy adult human liver synthesizes 8–10 grams of GSH daily. Normally, there is an appreciable flow of GSH from liver into plasma. The major organs involved in the inter-organ transport of GSH are the liver and the kidney, which is the primary organ for clearance of circulating GSH. It has been estimated to account for 50–67% of net plasma GSH turnover. Several investigators have found that during a single pass through the kidney, 80% or more of the plasma GSH is extracted, greatly exceeding the amount which could be accounted for by glomerular filtration. While the filtered GSH is degraded stepwise by the action of the brush-border enzymes γ-glutamyltransferase and cysteinyglycine dipeptidase, the remainder of the GSH appears to be transported via an unrelated, Na+-dependent system present in basal-lateral membranes.

GSH transported from hepatocytes interacts with the transpeptidase of ductile cells, and there appears to be a substantial reabsorption of metabolites by ductule endothelium. In the rat, about 12 and 4 nmoles/g/min of GSH appear in the hepatic vein and bile, respectively. Glutathione exists in plasma in four forms: reduced glutathione (GSH), oxidized glutathione (GSSG), mixed disulfide with cysteine (CySSG) and protein bound through a sulfhydryl linkage (GSSPr). The distribution of glutathione equivalents is significantly different than that of cyst(e)ine, and when either GSH or cysteine is added at physiological concentration, a rapid redistribution occurs. The distribution of glutathione equivalents in rat plasma is 70.0% protein bound, with the remaining 30% apportioned as follows: 28.0% GSH, 9.5% GSSG, and 62.6% as the mixed disulfide with cysteine. The distribution of cysteine equivalents was found to be 23% protein bound, with the remaining 77% distributed as follows: 5.9% cysteine, 83.1% cystine, and 10.8% as the mixed disulfide with glutathione. Plasma thiols and disulfides are not in equilibrium, but appear to be in a steady state maintained in part by transport of these compounds between tissues during the interorgan phase of their metabolism. The large amounts of protein-bound glutathione and cysteine provide substantial buffering which must be considered in the analysis of transient changes in glutathione and cysteine. This buffering may protect against transient thiol-disulfide redox changes which could affect the structure and activity of plasma and plasma membrane proteins. In erythrocytes, GSH has been implicated in reactions which maintain the native structure of hemoglobin and of enzymes and membrane proteins. GSH is represent in erythrocytes at levels 1000 times greater than in plasma. It functions as the major small molecule antioxidant defense against toxic free radicals, an inevitable by-product of the erythrocytes' handling of $O_2$.

Glutathione and the Immune System

The importance of thiols and especially of GSH to lymphocyte function has been known or many years. Adequate concentrations of GSH are required for mixed lymphocyte reactions, T-cell proliferation, T- and B-cell differentiation, cytotoxic T-cell activity, and natural killer cell activity. Adequate GSH levels have been shown to be necessary for microtubule polymerization in neutrophils. Intraperitoneally administered GSH augments the activation of cytotoxic T-lymphocytes in mice, and dietary GSH was found to improve the splenic status of GSH in aging mice, and to enhance T-cell-mediated immune responses.

The presence of macrophages can cause a substantial increase of the intracellular GSH levels of activated lymphocytes in their vicinity. Macrophages consume cystine via a strong membrane transport system, and generate large amounts of cysteine which they release into the extracellular space. It has been demonstrated that macrophage GSH levels (and therefore cysteine equivalents) can be augmented by exogenous GSH. T-cells cannot produce their own cysteine, and it is required by T-cells as the rate-limiting precursor of GSH synthesis. The intracellular GSH level and the DNA synthesis activity in mitogenically-stimulated lymphocytes are strongly increased by exogenous cysteine, but not cystine. In T-cells, the membrane transport activity for cystine is ten-fold lower than that for cysteine. As a consequence, T-cells have a low baseline supply of cysteine, even under healthy physiological conditions. The cysteine supply function of the macrophages is an important part of the mechanism which enables T-cells to shift from a GSH-poor to a GSH-rich state.

The importance of the intracellular GSH concentration for the activation of T-cells is well established. It has been reported that GSH levels in T-cells rise after treatment with GSH; it is unclear whether this increase is due to uptake of the intact GSH or via extracellular breakdown, transport of breakdown products, and subsequent intracellular GSH synthesis. Decreasing GSH by 10–40% can completely inhibit T-cell activation in vitro. Depletion of intracellular GSH has been shown to inhibit the mitogenically-induced nuclear size transformation in the early phase of the response. Cysteine and GSH depletion also affects the function of activated T-cells, such as cycling T-cell clones and activated cytotoxic T-lymphocyte precursor cells in the late phase of the allogenic mixed lymphocyte culture. DNA synthesis and protein synthesis in IL-2 dependent T-cell clones, as well as the continued growth of preactivated CTL precursor cells and/or their functional differentiation into cytotoxic effector cells are strongly sensitive to GSH depletion.

The activation of physiologic activity of mouse cytotoxic T-lymphocytes in vivo was found to be augmented by interperitoneal (i.p.) GSH in the late phase but not in the early phase of the response. The injection of GSH on the third day post immunization mediated a 5-fold augmentation of cytotoxic activity. Dietary GSH supplementation can reverse age-associated decline of immune response in rats, as demonstrated by maintenance of Concanavalin A stimulated proliferation of splenocytes in older rats.

Glutathione status is a major determinant of protection against oxidative injury. GSH acts on the one hand by reducing hydrogen peroxide and organic hydroperoxides in reactions catalyzed by glutathione peroxidases, and on the other hand by conjugating with electrophilic xenobiotic intermediates capable of inducing oxidant stress. The epithelial cells of the renal tubule have a high concentration of GSH, no doubt because the kidneys function in toxin and waste elimination, and the epithelium of the renal tubule is exposed to a variety of toxic compounds. GSH, transported into cells from the extracellular medium, substantially protects isolated cells from intestine and lung are against t-butylhydroperoxide, menadione or paraquat-induced toxicity. Isolated kidney cells also transport GSH, which can supplement endogenous synthesis of GSH to protect against oxidant injury. Hepatic GSH content has also been reported to rise, indeed to double, in the presence of exogenous GSH. This may be due either to direct transport, as has been reported for intestinal and alveolar cells, or via extracellular degradation, transport, and intracellular resynthesis.

The nucleophilic sulfur atom of the cysteine moiety of GSH serves as a mechanism to protect cells from harmful effects induced by toxic electrophiles. The concept that glutathione S-conjugate biosynthesis is an important mechanism of drug and chemical detoxification is well established. GSH conjugation of a substrate generally requires both GSH and glutathione-S-transferase activity. The existence of multiple glutathione-S-transferases with specific, but also overlapping, substrate specificities enables the enzyme system to handle a wide range of compounds.

Several classes of compounds are believed to be converted by glutathione conjugate formation to toxic metabolites. Halogenated alkenes, hydroquinones, and quinones have been shown to form toxic metabolites via the formation of S-conjugates with GSH. The kidney is the main target organ for compounds metabolized by this pathway. Selective toxicity to the kidney is the result of the kidney's ability to accumulate intermediates formed by the processing of S-conjugates in the proximal tubular cells, and to bioactivate these intermediates to toxic metabolites.

The administration of morphine and related compounds to rats and mice results in a loss of up to approximately 50% of hepatic GSH. Morphine is known to be biotransformed into morphinone, a highly hepatotoxic compound, which is 9 times more toxic than morphine in mouse by subcutaneous injection, by morphine 6-dehydrogenase activity. Morphinone possesses an $\alpha,\beta$-unsaturated ketone, which allows it to form a glutathione S-conjugate. The formation of this conjugate correlates with loss of cellular GSH. This pathway represents the main detoxification process for morphine. Pretreatment with GSH protects against morphine-induced lethality in the mouse.

The deleterious effects of methylmercury on mouse neuroblastoma cells are largely prevented by coadministration of GSH. GSH may complex with methylmercury, prevent its transport into the cell, and increase cellular antioxidant capabilities to prevent cell damage. Methylmercury is believed to exert its deleterious effects on cellular microtubules via oxidation of tubulin sulfhydryls, and by alterations due to peroxidative injury. GSH also protects against poisoning by other heavy metals such as nickel and cadmium.

Because of its known role in renal detoxification and its low toxicity, GSH has been explored as an adjunct therapy for patients undergoing cancer chemotherapy with nephrotoxic agents such as cisplatin, in order to reduce systemic toxicity. In one study, GSH was administered intravenously to patients with advanced neoplastic disease, in two divided doses of 2,500 mg, shortly before and after doses of cyclophosphlamide. GSH was well-tolerated and did not produce unexpected toxicity. The lack of bladder damage, including microscopic hematuria, supports the protective role of this compound. Other studies have shown that i.v. GSH coadministration with cisplatin and/or cyclophosphamide combination therapy, reduces associated nephrotoxicity, while not unduly interfering with the desired cytotoxic effect of these drugs.

Clinical Use of Glutathione

Ten elderly patients with normal glucose tolerance and ten elderly patients with impaired glucose tolerance (IGT) underwent GSH infusion, 10 mg/min for 120 min, for a total dose of 1,200 mg in 2 hr, under basal conditions and during 75 g oral glucose tolerance tests and intravenous glucose tolerance tests. Basal plasma total glutathione levels were essentially the same for normal and IGT groups, and GSH infusion under basal conditions increased GSH to similar levels. This study demonstrated that GSH significantly potentiated glucose-induced insulin secretion in patients with IGT. No effect was seen on insulin clearance and action.

The antihypertensive effect of an i.v. bolus of 1,844 mg. or 3,688 mg. GSH was studied in normal and mild to moderate essential hypertensive subjects and in both hypertensive and non-hypertensive diabetics, both type I and type II. The administration of 1,844 mg. GSH produced a rapid and significant decrease in both systolic and diastolic blood pressure, within ten minutes, but which returned to baseline within 30 minutes, in both groups of hypertensive patients and in non-hypertensive diabetics, but had no effect in normal healthy subjects. At the 3,699 mg. dose, not only did the blood pressure decrease in the hypertensive subjects, but GSH produced a significant decrease in the blood pressure values in normal subjects as well.

GSH, 1,200 mg/day intravenously administered to chronic renal failure patients on hemodialysis was found to significantly increase studied hematologic parameters (hematocrit, hemoglobin, blood count) as compared to baseline, and holds promise to reverse the anemia seen in these patients.

Toxicological Effects of Glutathione

The reported $LD_{50}$ of GSH in rats and mice via various routes of administration are listed in the table below. GSH has an extremely low toxicity, and oral $LD_{50}$ measurements are difficult to perform due to the sheer mass of GSH which has to be ingested by the animal in order to see any toxic effects.

adverse effects were reported. No evidence of toxicities from laboratory studies or from clinical examinations was reported; however, no benefit was conclusively demonstrated.

Pharmacokinetics of Glutathione

The pharmacokinetics of intravenously administered GSH were determined in the rat and interpreted by means of an open, two-compartment model. Following a bolus injection of 50–300 mmol/kg GSH, arterial plasma concentrations of (i) GSH, (ii) oxidized glutathione/GSSG, (iii) total thiols, and (iv) soluble thiols minus GSH, were elevated and then rapidly decreased non-exponentially, as anticipated. With increasing dose, the rate constant for drug elimination and plasma clearance increased form 0.84 to 2.44 mL/min. and the half-life of the elimination phase decreased from 52.4 to 11.4 minutes. Both the apparent volume of distribution and the degree of penetration of GSH into the tissues

| Animal | Route of Admin. | $LD_{50}$ | Reference |
|---|---|---|---|
| Mouse | Oral | 5000 mg/kg | Modern Pharmaceuticals of Japan, IV Edition, Tokyo, Japan Pharmaceutical, Medical and Dental Supply Exporters' Association, 1972, p 93. |
| Mouse | Intraperitoneal | 4020 mg/kg | Modern Pharmaceuticals of Japan, IV Edition, Tokyo, Japan Pharmaceutical, Medical and Dental Supply Exporters' Association, 1972, p 93. |
| Mouse | Intraperitoneal | 6815 mg/kg | Toxicology, vol. 62, P. 205, 1990. |
| Mouse | Subcutaneous | 5000 mg/kg | Modern Pharmaceuticals of Japan, IV Edition, Tokyo, Japan Pharmaceutical, Medical and Dental Supply Exporters' Association, 1972, p 93. |
| Mouse | Intravenous | 2238 mg/kg | Japanese J. of Antibiotics, vol. 38, p. 137, 1985. |
| Mouse | Intramuscular | 4000 mg/kg | Modern Pharmaceuticals of Japan, III Edition, Tokyo, Japan Pharmaceutical, Medical and Dental Supply Exporters' Association, 1968, p 97. |

GSH can be toxic, especially in cases of ascorbate deficiency, and these effects may be demonstrated in, for example, ascorbate deficient guinea pigs given 3.75 mmol/kg daily (1,152 mg/kg daily) in three divided doses, whereas in non-ascorbate deficient animals, toxicity was not seen at this dose, but were seen at double this dose.

Use of High-Dose Oral GSH in Cancer Patients

In one published study, eight patients with hepatocellular carcinoma were treated with 5 g oral reduced glutathione per day. Two patients withdrew shortly after receiving GSH due to intolerable side-effects (gastrointestinal irritation and sulfur odor). The remaining patients, aged 27–63, three male and three female, did not experience side-effects from this high dose of GSH and continued to take 5 g oral GSH for periods ranging from 119 days (at which time the patient died from her tumor) to >820 days (this patient was still alive at the time of publication and was still taking 5 g oral GSH daily; his tumor had not progressed and his general condition was good). Two of the female patients survived 1 year and exhibited regression or stagnation of their tumor growth. The remaining two patients, both male, died as expected within 6 months.

Experience in HIV-Infected Patients

A commercially available nutritional formulation containing 3 grams of reduced glutathione was given daily to a group of 46 AIDS patients for a period of three months by a group of private physicians. No significant GSH-related were diminished with increasing dose (from 3.78 to 1.33 L/Kg and from 6.0 to 0.51 as $k_{12}/k_{21}$, respectively). The data indicate that GSH is rapidly eliminated. This is mainly due to rapid oxidation in plasma rather than by increased tissue extraction or volume distribution. Thus, plasma GSH levels appear to be quickly regulated by which the body may maintain concentrations within narrow physiological limits.

When single doses of 600 mg GSH were administered intravenously to sheep, GSH levels in venous plasma and lung lymph rose transiently. The mean concentration was approximately 50 mM for venous plasma, peaking at 30 min, and returning to baseline after 45 minutes. Lung lymph peak level was about 100 mM at 15 min, returning to baseline after 30 minutes. Average epithelial lining fluid (ELF) levels were variable but showed no significant increase over baseline during the three hour observation period. Urine excretion was rapid with peak levels at 15 minutes. In both plasma and lung lymph, GSH accounted for greater than 95% of the total glutathione (GSH plus GSSG). In ELF 75.4% of the baseline glutathione was in the reduced form, whereas in urine 59.6% was present as GSH.

Orally ingested reduced glutathione is absorbed intact from the small intestine in a rat model, specifically in the upper jejunum. It is noted that rat metabolism differs from man, and therefore the results of rat studies should be verified in man before the results are extrapolated. Plasma GSH concentration in rats increased from 15 to 30 mM after administration of GSH either as a liquid bolus (30 mM) or mixed (2.5–50 mg/g) in AIN-70 semi-synthetic diet (11). GSH concentration was maximal at 90–120 minutes after GSH administration and remained high for over 3 hours. Administration of the amino acid precursors of GSH had little or no effect on plasma GSH values, indicating that GSH catabolism and re-synthesis do not account for the increased GSH concentration seen. Inhibition of GSH synthesis and degradation by L-buthionine-[S,R]-sulfoximine (BSO) and acivicin showed that the increased plasma GSH came mostly from absorption of intact GSH instead of from its metabolism. Plasma protein-bound GSH also increased after GSH administration, with a time course similar to that observed for free plasma GSH. Thus, dietary GSH can be absorbed intact and results in a substantial increase in blood plasma GSH.

Administration of oral GSH increased hepatic glutathione levels in: (i) rats fasted 48 hours, (ii) mice treated with GSH depletors, and (iii) mice treated with paracetamol (a drug which promotes a depletion of hepatic GSH followed by hepatic centrilobular necrosis). In these experiments, the animals were orally intubated with 1000 mg/kg body weight GSH. Mean pretreatment values in 48-hour fasted rats were 3.0–3.1 mmol/g fresh hepatic tissue. Mean values after treatment were 5.8, 4.2, and 7.0 mmol/g fresh hepatic tissue for 2.5, 10, and 24 hours post-treatment, respectively. Mice were given an oral dose of GSH (100 mg/kg) and concentrations of GSH were measured at 30, 45 and 60 min in blood plasma and after 1 hr in liver, kidney, heart, lung, brain, small intestine and skin. GSH concentrations in plasma increased from 30 mM to 75 mM within 30 min of oral GSH administration, consistent with a rapid flux of GSH from the intestinal lumen to plasma. No increases over control values were obtained in most tissues except lung over the same time course. Mice pretreated with the GSH synthesis inhibitor BSO had substantially decreased tissue concentrations of GSH, and oral administration of GSH to these animals resulted in statistically-significant increases in the GSH concentrations of kidney, heart, lung, brain, small intestine and skin but not in liver.

The kinetics and the effect of glutathione on plasma and urine sulphydryls were studied in ten healthy human volunteers. Following the intravenous infusion of 2000 g/m$^2$ of GSH the concentration of total glutathione in plasma increased from 17.5–13.4 mmol/Liter (mean =/–SD) to 823–326 mmol/Liter. The volume of distribution of exogenous glutathione was 176–107 Ml/Kg and the elimination rate constant was 0.063–0.027/minute, corresponding to a half-life of 14.1–9.2 minutes. Cysteine in plasma increased from 8.9–3.5 mmol/Liter to 114–45 mmol/Liter after the infusion. In spite of the increase in cysteine, the plasma concentration of total cyst(e)ine (i.e. cysteine, cystine, and mixed disulphides) decreased, suggesting an increased uptake of cysteine from plasma into cells. The urinary excretion of glutathione and of cyst(e)ine was increased 300-fold and 10-fold respectively, in the 90 minutes following the infusion.

Normal healthy volunteers were given an oral dose of GSH to determine whether dietary GSH could raise plasma GSH levels. Results showed that an oral dose of GSH (15 mg/kg) raised plasma glutathione levels in humans 1.5–10 fold over the basal concentration in four out of five subjects tested, with a mean value three times that of normal plasma GSH levels. Plasma GSH became maximal 1 hour after oral administration, dropping to approximately ½ maximal values after three hours. Equivalent amounts of GSH amino acid constituents failed to increase plasma levels of GSH. GSH bound to plasma proteins also increased with the same time course as seen with free GSH.

SUMMARY OF THE INVENTION

The present inventors have found that oral glutathione bioavailability and efficiency may be increased by the administration of pharmaceutically stabilized reduced glutathione in a bolus on an empty stomach.

The present inventors have also found that glutathione is efficiently absorbed from mucous membranes, especially the sublingual mucosa and lumen of the duodenum and initial part of the ileum.

As used herein, the term "pharmaceutically stabilized glutathione" refers to glutathione which is maintained in a reduced form without substantial cyclization. This stabilization may be effected by the addition of one or more agents which, together with the glutathione, provide a pharmaceutical formulation which is capable of delivering native reduced glutathione.

The present invention also includes novel combinations of glutathione and other pharmacological agents and in novel dosage forms and means for administration.

The oral administration of pharmaceutically stabilized reduced glutathione, presented as a charge transfer complex in relatively high concentration may produce a significant, predictable increase in intracellular glutathione levels in humans.

BRIEF DESCRIPTION OF THE DRAWINGS AND APPENDICES

The invention is shown by way of example in the drawings, in which:

FIG. 1 shows a graph of a clinical response of an HIV infected subject to 1 gram of administered glutathione; and FIG. 2 shows a table of clinical study results.

DETAILED DESCRIPTION OF THE PREFERRED EMBODIMENTS

It has been found that, in otherwise healthy HIV infected humans, the intracellular glutathione levels in the peripheral blood mononucleocytes (PBMs) was significantly increased after oral administration of stabilized glutathione. This is achieved by providing a glutathione formulation which ensures delivery of adequate dose of pharmaceutically stabilized, reduced glutathione, with rapid dissolution before the duodenum. The formulation is administered to efficiently provide a high concentration of glutathione in the duodenum, i.e., on an empty stomach, to enhance uptake.

A preferred formulation includes 250 mg. or more of reduced glutathione with at least equimolar ascorbic acid, to fulfill three functions: acts as a sacrificial non-specific antioxidant during preparation, storage and after ingestion; reduces or neutralizes static electrical charge of glutathione powder, allowing dense packing of capsules; and acts as a lubricant for the encapsulation device. The ascorbic acid also maintains an acidic and reducing environment, which pharmaceutically stabilizes the glutathione molecule. Ascorbic acid is believed to form a charge couple with glutathione which enhances penetration through cell membranes, and reduces the tendency for the gamma-glutamyl and glycinyl residues to assume a cyclic conformation or to form an internal cyclic amide. The ascorbate thus complexes with the glutathione in solution to maintain a linear conformation. This linear conformation, in turn, stericly hinders the free cysteinyl thiol group. This steric hindrance stabilizes a free radical which may be formed, and thus maintains the biological activity of glutathione.

A cyclic form of glutathione, which may occur under certain conditions, such as neutral to basic pH, exposes the sulfhydryl moiety, making it more reactive. Under alkaline pH, cyclic amide formation is promoted, leaving a potentially toxic compound. The cyclic glutathione composition is a potential structural analog which may inhibit glutathione reductase, glutathione peroxidase and specific glutathione transporter proteins.

Likewise, oxidizing conditions promote disulfide formation (GSSG and Pr—S—S—G), which may reduce bioavailability of glutathione and counteract some of the potential benefits of glutathione administration. Further, oxidizing conditions also promote desulfuration, resulting in opthalmic acid formation (or other compounds), which may be toxic or inhibit efficient glutathione absorption.

A preferred oral formulation thus preferably includes an effective amount of glutathione mixed with a stabilizing agent, which is administered under such conditions that the concentration of glutathione attained in the lumen of the latter portion of the duodenum is higher than the plasma glutathione concentration, and preferably higher than the intercellular concentration of the epithelial lining cells. Thus, for example, a glutathione and ascorbic acid capsule is taken on an empty stomach. The reducing agent, preferably ascorbic acid, prevents oxidation of the glutathione during packaging and storage, and further may stabilize the glutathione in the relatively alkaline conditions of the duodenum prior to absorption. Desulfuration of glutathione leads to the formation of ophthalmic acid, the serine analog of glutathione, which inhibits glutathione uptake. This protocol is in contrast to prior art administration methods, which direct taking glutathione capsules after meals. By diluting glutathione with food, degradative enzymes are diluted and alkaline conditions buffered; however, according to the present invention, the rapidity of absorption allows high bioavailability with only a small amount of degradation.

The present invention also advantageously provides a method of use and pharmaceutical formulation of glutathione combined and another pharmaceutically active composition, wherein the other composition is selected from a broad group consisting of:

easily oxidized compositions, antioxidant compositions, compositions with oxidant effects, compositions for the treatment of pathology associated with:

suppressed total glutathione levels, suppressed reduced glutathione levels, relatively oxidized conditions in the organism, uncontrolled free radical or oxidizing reactions, or conditions where a more reduced state is desirable.

Glutathione may be used alone or in combination with other known compositions for the treatment or palliation of AIDS, HIV infection or retroviral replication (e.g., HTLV I, HTLV-II, HTLV-III, etc.), herpes virus replication (e.g., Herpes simplex type I, Herpes simplex type II, Herpes zoster (varicella), CMV, EBV, HHV-8, etc.), rabies, ebola virus, influenza virus, CHF, coronary artery disease, status post coronary artery restenosis, Diabetes mellitus, Macular Degeneration, and/or hepatitis (toxic or infectious).

Glutathione may also be used, alone or in combination with other therapies for the treatment of free radical associated neurological conditions, for example, Alzheimer's disease, Parkinson's disease, catecholamine toxicities, other free-radical associated toxicities, stroke and transient ischemic events, spinal chord injury and other traumatic injuries to nerve tissue, peripheral neuropathics, possibly prion-associated illness, infectious agent pathology and inflammatory pathology, or to reduce the free-radical associated toxicity of drugs administered to treat these conditions.

Mycoplasma infections, such as mycoplasma pneumonia, are believed to cause pathology due to free radical reactions within cells by these intracellular parasites. Therefore, glutathione may be administered alone or in combination with an anti-mycoplasma antibiotic for the treatment of mycoplasma infections.

The present invention may also be used to increase or supplement the glutathione levels in normal mammals. This may be desired, for example, for prophylaxis against ischemic events, free radical damage from sun, chemicals, or other environmental exposure, and to reduce a cancer risk.

In fact, since oxidizing conditions in an organism are generally undesirable, and where necessary the mechanisms for producing oxidizing conditions typically overpower ingested antioxidants, a large number of medications and drugs are appropriate for combination with glutathione. However, certain conditions may require care in the administration of glutathione. Further, certain cancer chemotherapy regimens rely on exhaustion of cellular free radical quenching mechanisms to selectively kill target cells. Finally, cellular apoptosis, or programmed cell death, relies on exhaustion of reduced glutathione levels in cells (mitochondria), resulting in death. Where this mechanism is required or physiologically correct, interruption by exogenous glutathione may be undesirable. Further, glutathione may interact with some compositions, either to non-specifically reduce or combine with the chemical moiety, or to alter a metabolism after ingestion; unless accounted for, these effects may be undesirable.

A known anti-HIV therapy, 3'-azidothymidine (zidovudine, AZT), acts as a potent reverse transcriptase inhibitor. This drug, however, generates free radicals and is toxic to mitochonidria, and is associated with a myopathy. Glutathione may therefore be administered in conjunction with AZT to reduce toxicity while not interfering with the reverse transcriptase inhibitory activity, thus increasing the therapeutic index. Likewise, glutathione may also be used to increase the therapeutic index of other drugs which have a significant free-radical associated toxicity.

There are a number of conditions which are believed to be associated with reduced intracellular antioxidant levels, including AIDS, diabetes, macular degeneration, congestive heart failure, vascular disease and coronary artery restenosis, Herpes virus infection, toxic and infectious hepatitis, and rabies. Certain interstitial lung disease may be due to insufficient glutathione levels. Further, various toxins and medications may also result in free radical reactions, including types of cancer chemotherapy. Therefore, the present invention holds potential to treat these diseases and conditions by the use of a convenient, effective oral formulation of glutathione. Thus, the administration of exogenous glutathione supplements the hepatic output to help maintain reduced conditions within the organism. As noted above, the failure to quench free radical reactions allows an undesirable cascade resulting in damage to macromolecules, lipid peroxidation, and generation of toxic compounds. The maintenance of adequate glutathione levels is necessary to block these free radical reactions.

Glutathione also has the ability to form complexes with metals. For example, as discussed above, glutathione forms chelation complexes with nickel, lead, cadmium, mercury, vanadium and manganese. Glutathione also forms circulating complexes with copper in the plasma. According to the present invention, glutathione may be administered to treat metal toxicity. It is believed that the glutathione-metal complexes will be excreted, thus reducing the metal load. Thus, glutathione may be administered for the treatment of toxicity associated with iron, copper, nickel, lead, cadmium, mercury, vanadium, manganese, cobalt, transuranic metals, such as plutonium, uranium, polonium, and the like. As compared to EDTA, glutathione has a reduced tendency to chelate calcium, providing a significant advantage. It is noted that the chelation properties of glutathione are separate from the antioxidant properties; however, some metal toxicities are free radical mediated, for example iron, and therefore glutathione administration for these conditions is particularly advantageous.

In order to provide high bioavailability, it has been found desirable to provide a relatively high concentration of reduced glutathione in proximity to the mucous membrane, e.g., the duodenum for oral administration. Thus, in contrast to prior methods, the glutathione is preferably administered as a single bolus on an empty stomach. The preferred dosage is between about 100–10,000 mg. glutathione, and more preferably between about 250–3,000 mg. glutathione. Further, the glutathione formulation is preferably stabilized with a reducing agent (antioxidant), preferably ascorbic acid, to reduce oxidation both during storage and in the digestive tract prior to absorption. The use of crystalline ascorbic acid has the added benefit of reducing the static charge of glutathione for improved encapsulation and serving as a lubricant for the encapsulation apparatus. However, other static dissipation methods or additives may be employed, and other antioxidants may be employed. The preferred dosage form is a capsule, e.g., a two-part gelatin capsule, which protects the glutathione from air and moisture, while dissolving quickly in the stomach.

The digestive tract is believed to have specific facilitated or active transport carriers for glutathione which allow uptake of glutathione from the intestinal lumen without degradation. According to the present invention, the uptake through this mechanism is maximized by providing a high concentration gradient and avoiding the presence or production of transport inhibitors, such as ophthalmic acid. Thus, the preferred method of oral administration according to the present invention employs an uptake mechanism which differs.

The oral mucosa have been found to allow rapid and efficient uptake of glutathione into the blood. In contrast to the digestive tract, the significance of facilitated or active transport mechanisms in the oral mucosa is believed to be low; rather, a high concentration of glutathione in the oral mucosa is believed to permit passive transport of the glutathione through the cells or around the cells into the capillary circulation. Therefore, compositions intended for absorption through the oral mucosa, e.g., for sublingual administration, are preferably of high purity, as contaminants may be absorbed similarly to glutathione, and as relatively small, uncharged molecules. Therefore, the composition preferably includes ascorbic acid which helps to maintain the glutathione in a reduced state, maintains a somewhat acidic environment in the mouth to avoid deprotonation of the glutamic acid residue, without causing substantially all of the amines to be protonated.

It has been found, contrary to reports of other scientists, that glutathione is not substantially degraded in the stomach, and therefore, the release of the glutathione need not diluted in the stomach or release be delayed. In fact, according to the present invention, the glutathione formulation is preferably released and dissolved in the stomach. The addition of stabilizer, i.e., ascorbic acid, further improves the ability of the glutathione to reach its site of absorption in the intestine undegraded. Once past the stomach, it is important that the glutathione be immediately available for absorption, as the desulfurases and peptidases from the pancreas, as well as the increase in pH, do tend to degrade the glutathione. The desulfurase produces ophthalmic acid, which interferes with glutathione absorption. Thus, by providing a high concentration of glutathione in the duodenum, without substantial dilution, the glutathione may be absorbed at a maximum rate. While the degradation of glutathione in the latter part of the duodenum and ileum may compete with the absorption process, the present method provides significant bioavailability. In fact, studies have demonstrated about 90% bioavailability of orally administered glutathione according to the present invention.

The capsule is preferably a standard two-part hard gelatin capsule of double-O (OO) size, which may be obtained from a number of sources. After filling, the capsules are preferably stored under nitrogen, to reduce oxidation during storage. The capsules are preferably filled according to the method of U.S. Pat. No. 5,204,114, incorporated herein by reference in its entirety, using crystalline ascorbic acid as both an antistatic agent and stabilizer. Further, each capsule preferably contains 500 mg of glutathione and 250 mg of crystalline ascorbic acid. A preferred composition includes no other excipients or fillers; however, other compatible fillers or excipients may be added. While differing amounts and ratios of glutathione and stabilizer may be used, these amounts are preferable because they fill a standard double-O capsule, and provide an effective stabilization and high dose. Further, the addition of calcium carbonate, a component of known high dose glutathione capsules, is avoided as there may be impurities in this component. Further, calcium carbonate acts as a base, neutralizing stomach acid, which accelerates degradation of glutathione in the small intestine.

Because the glutathione and ascorbic acid are administered in relatively high doses, it is preferred that these components be highly purified, to eliminate impurities, toxins or other chemicals, which may destabilize the formulation or produce toxic effects or side effects. As stated above, the formulation may also include other pharmaceutical agents, of various classes.

Glutathione is advantageously administered over extended periods. Therefore, one set of preferred useful combinations include glutathione and drugs intended to treat chronic conditions which are well absorbed on an empty stomach, and do not have adverse interactions or reduced or variable combined absorption.

One particular class of drugs includes central or peripheral adrenergic or catecholenergic agonists, or reuptake blockers, which may produce a number of toxic effects, including neurotoxicity, cardiomyopathy and other organ damage. These drugs are used, for example, as cardiac, circulatory and pulmonary medications, anesthetics and psychotropic/antipsychotic agents. Some of these drugs also have abuse potential, as stimulants, hallucinogens, and other types of psychomimetics. Other free radical initiation associated drugs include thorazine, tricyclic antidipressants, quinolone antibiotics, benzodiazepines, acetaminphen and alcohol.

Therefore, it is an aspect of the present invention to provide an oral pharmaceutical formulation comprising glutathione in an amount of between about 50–10,000 mg, and an effective amount of a pharmacological agent capable of initiating free radical reactions in a mammal. The pharmacological agent is, for example, an adrenergic, dopaminergic, serotonergic, histaminergic, cholinergic, gabaergic, psychomimetic, quinone, quinolone, tricyclic, and/or steroid agent.

Hepatic glutathione is consumed in the metabolism, catabolism and/or excretion of a number of agents. The depletion of hepatic glutathione may result in hepatic damage or a toxic hepatitis. Such agents may include, for example, aminoglycoside antibiotics, acetominophen, morphine and other opiates. High dose niacin, used to treat hypercholesterolemia, has also been associated with a toxic hepatitis. The present invention therefore encompasses an oral pharmaceutical formulation comprising glutathione in an amount of between about 50–10,000 mg, administered in conjunction with and an effective amount of a pharmacological agent which consumes hepatic glutathione reserves.

A number of pathological conditions result in hepatic damage. This damage, in turn, reduces the hepatic reserves of glutathione and the ability of the liver to convert oxidized glutathione to its reduced form. Other pathological conditions are associated with impaired glutathione metabolism. These conditions include both infectious and toxic hepatitis, cirrhosis, hepatic primary and metastatic carcinomas, traumatic and iatrouenic hepatic damage or resection. The present invention encompasses a pharmaceutical formulation comprising glutathione and an antiviral or antineoplastic agent. The antiviral or antineoplastic agent is, for example, a nucleoside analog.

Glutathione is broken down, and cysteine excreted, possibly in the urine. Very high doses of glutathione may therefore result in cysteinuria, which may result in cysteine stones. Other long, term toxicity or adverse actions may result. Therefore, a daily intake of greater than about 10 gm. for extended period should he medically monitored. On the other hand, individual doses below about 50 mg. are insufficient to raise the concentration of the duodenal lumen to high levels to produce high levels of absorption, and to provide clinical benefit. Therefore, the preferred formulations according to the present invention have glutathione content greater than 50 mg, and provided in one or more doses totaling up to about 10,000 mg per day.

In the treatment of HIV infection, it is believed that the oral administration of a relatively high dose bolus of glutathione, i.e., 1–3 grams per day, on an empty stomach, will have two beneficial effects. First, HIV infection is associated with a reduction in intracellular glutathione levels in PBMs, lung, and other tissues. It is further believed that by increasing the intracellular glutathione levels, that the functioning, of these cells may be returned to normal. Therefore, the administration of glutathione according to the present invention will treat the effects of HIV infection. Therefore, the present invention encompasses the oral administration of glutathione and ascorbic acid, optionally in combination with an antiretroviral agent. It is noted that the transcription mechanisms and control involved in retroviral infection is believed to be relatively conserved between various types. Therefore, late stage retroviral suppression is expected for the various types of human retroviruses and analogous animal retroviruses.

Second, it has been found in in vitro tests that by increasing the intracellular levels of glutathione in infected monocytes to the high end of the normal range, the production of HIV from these cells may be suppressed for about 35 days. This is believed to be related to the interference in activation of cellular transcription by cytokines, including NFkB and TNFα. Therefore, the infectivity of HIV infected persons may be reduced, helping to prevent transmission. This reduction in viral load may also allow the continued existence of uninfected but susceptible cells in the body.

Glutathione, administered according to the present method, is believed to be effective in the treatment of congestive heart failure (CHF). In CHF, there are believed to be two defects. First, the heart muscle is weakened, causing enlargement of the heart. Second, peripheral vasospasm is believed to be present, causing increased peripheral resistance. Glutathione is effective in enhancing the effects of nitric oxide, and therefore is believed to be of benefit to these patients by decreasing vasoconstriction and peripheral vascular resistance, while increasing blood flow to the tissues. While nitroso-glutathione is more effective at preventing platelet aggregation than at vasodilation, it is nevertheless a potent vasodilator with a longer half-life than nitric oxide alone. Further, since a relative hypoxia of the tissues is associated with free radical-mediated cellular damage, the presence of glutathione will also help to block this damage. The present invention therefore encompasses the oral administration of glutathione in conjunction with a congestive heart failure medication, for example, digitalis glycosides. dopamine, methyldopa, phenoxybenzamine, dobutamine, terbutaline, amrinone, isoproterenol, beta blockers, calcium channel blockers, such as verapamil, propranolol, nadolol, timolol, pindolol, alprenolol, oxprenolol, sotalol, metoprolol, atenolol, acebutolol, bevantolol, tolamolol, labetalol, diltiazem, dipyridamole, bretylium, phenytoin, quinidine, clonidine, procainamide, acecainide, amiodarione, disopyramide, encainide, flecanide, lorcainide, mexiletine, tocainide, captopril, minoxodil, nifedipine, albuterol, pargyline, vasodilators, including nitroprusside, nitroglycerin, phentolamine, phenoxybenzamine, hydrazaline, prazosin, trimazosin, tolazoline, trimazosin, isosorbide dinitrate, erythrityl tetranitrate, asprin, papaverine, cyclandelate, isoxsuprine, niacin, nicotinyl alcohol, nylidrin, diuretics, including furosemide, ethacrynic acid, spironolactone, triamterine, amiloride, thiazides, bumetanide, caffeine, theophylline, nicotine, captopril, salalasin, and potassium salts.

It has been found that elevated levels of homocysteine as a significant risk in vascular disease, such as atherosclerosis, venous thrombosis, heart attack and stroke, as well as neural tube defects and neoplasia. Moghadasian et al., "Homocyst(e)ine and Coronary Artery Disease", Arch, Int. Med. 157 (10):2299–2308 (Nov. 10, 1997), incorporated herein by reference. Homocystiene promotes free radical reactions. In patients with defective homocysteine metabolism, relatively high levels of homocysteine are present in the blood. According to the present invention, glutathione is administered to patients with elevated homocysteine levels.

It was believed that, because hepatocytes produce reduced glutathione through a feedback-inhibited pathway, that hepatocytes would not absorb reduced glutathione from the plasma. Therefore, an insult to hepatocytes, for example from toxic or infectious origin, which otherwise suppressed glutathione production would result in cellular damage or death. In fact, the present inventors believe that this is not the case, at least in the case of compromised hepatocytes. Therefore, it is an aspect according to the present invention to treat hepatitis, of various types, with oral glutathione. For example, both alcohol and acetaminophen are both hepatotoxic, and result in reduced hepatocyte glutathione levels. Therefore, these toxicities may be treated according to the present invention. Glutathione may also be effective in the treatment of other types of toxicities, to various cells or organs, which result in free radical damage to cells or reduced glutathione levels.

Diabetes, especially uncontrolled diabetes, results in glycosylation of various enzymes and proteins, which may impair their function or control. In particular, the enzymes which produce reduced glutathione (e.g., glutathione reductase) become glycosylated and non-functional. Therefore, diabetes is associated with reduced glutathione levels, and in fact, many of the secondary symptoms of diabetes may be attributed to glutathione metabolism defects. The present invention may therefore be applied to supplement diabetic patients with glutathione in order to prevent the major secondary pathology. The present invention also encompasses an oral pharmaceutical formulation comprising glutathione and an antihyperglycemic agent.

Glutathione, due to its strong reducing potential, breaks disulfide bonds. It is believed that most normal proteins are not denatured, to a great extent, by normal or superphysiologic levels of glutathione. It is believed, however, that opiate receptors are deactivated by high normal levels of glutathione. It is therefore believed that glutathione administration may be of benefit for the treatment of obesity and/or eating disorders, other addictive or compulsive disorders, including tobacco (nicotine) and opiate additions.

The present invention also encompasses the administration of glutathione in conjunction with nicotine. The physiologic effects of nicotine are well known. Glutathione, due to its vasodilatory effects, improves cerebral blood flow, resulting in a synergistic cerebral function-enhancing effect.

In mammals, the levels of glutathione in the plasma are relatively low, in the micromolar range, while intracellular levels are typically in the millimolar range. Therefore, the intracellular cytosol proteins are subjected to vastly higher concentrations of glutathione than extracellular proteins. The endoplasmic reticulum, a cellular organelle, is involved in processing proteins for export from the cell. It has been found that the endoplasmic reticulum forms a separate cellular compartment from the cytosol, having a relatively oxidized state as compared to the cytosol, and thereby promoting the formation of disulfide links in proteins, which are often necessary for normal activity. Hwang, C., et al., "Oxidized Redox State of Glutathione in the Endoplasmic Reticulum", Science 257:1496–1502 (Sept. 11, 1992), incorporated herein be reference. In a number of pathological states, cells may be induced to produce proteins for export from the cells, and the progression of the pathology interrupted by interference with the production and export of these proteins. For example, many viral infections rely on cellular production of viral proteins for infectivity. Interruption of the production of these proteins will interfere with infectivity. Likewise, certain conditions involve specific cell-surface receptors, which must be present and functional. In both these cases, cells which are induced to produce these proteins will deplete reduced glutathione in the endoplasmic reticulum. It is noted that cells which consume glutathione (GSH) will tend to absorb glutathione from the plasma, and may be limited by the amounts present. Therefore, by increasing plasma glutathione levels, even transiently, the reducing conditions in the endoplasmic reticulum may be interfered with, and the protein production blocked. Normal cells may also be subjected to some interference; however, in viral infected cells, or cells abnormally stimulated, the normal regulatory mechanisms may not be intact, and the redox conditions in the endoplasmic reticulum controlled by the availability of extracellular glutathione. In these conditions, the pharmaceutical administration of glutathione may produce significant effects.

Reproduction of herpes viruses, which are DNA viruses, is inhibited or reduced in cell culture by the administration of extracellular glutathione. Therefore, according to the present invention, herpes virus infections may be treated by administering glutathione according to the present invention. The known herpes viruses include herpes simplex virus I, herpes simplex virus II, herpes zoster, cytomegalovirus, Epstein Barr virus, as well as a number of other known viruses.

It is also believed that infection by the rabies virus, an RNA virus, may be treated by the administration of glutathione. While standard treatments are available, and indeed effective when timely administered, glutathione may be useful in certain circumstances. Therefore, rabies virus infection may be treated, at least in part, according to the present invention. One available treatment for rabies is an immune serum. The present invention therefore encompasses the parenteral administration of glutathione in combination with an antibody. Glutathione may also be administered separately.

Coronary heart disease risk is increased by the consumption of a high-fat diet, and reduced by the intake of antioxidant vitamins, including vitamin E and vitamin C, as well as flavonoids. High fat meals impair the endothelial function through oxidative stress, resulting in impaired nitric oxide availability. It has been found that vitamin C and vitamin E restores the vasoconstriction resulting from nitric oxide production by endothelium after a high fat meal. Plotnick, G. D. et al., "Effect of Antioxidant Vitamins on the Transient Impairment of Endothelium-Dependent Brachial Artery Vasoactivity Following a Single High Fat Meal", JAMA 278:1682–1686 (Nov. 26, 1997), incorporated herein by reference. According to the present invention, glutathione may be administered as a prophylaxis against vascular disease.

In utilizing antioxidants as advanced therapeutic approaches, the following principles have been developed over time:

Different disorders generate different types of free radicals, in different environments. Therefore, different specific antioxidants are needed for these various radicals and related compounds. The commonest species and related molecules includes superoxide, $\bullet O_2-$; hydroxyl, $\bullet OH$; peroxy, $\bullet OOH$; hydrogen peroxide, $H_2O_2$ (splitting into hydroxyl radicals); alkoxy, $RO\bullet$; delta singlet oxygen, $^1O_2$; nitric oxide, $\bullet NO$; lipid hydroperoxides, LOOH (splitting into alkoxy and hydroxyl radicals). See, Montaignier, Luc, Olivier, Rene, Pasquier, Catherine (Eds.), *Oxidative Stress in Cancer, AIDS, and Neurodegenerative Diseases*, Marcel Dekker, NY (1998), incorporated herein by reference in its entirety.

In addition to qualitative differences among several species of free radicals, their rates of formation will differ, as will the different types of inciting agents that may have to be simultaneously controlled. For example, continued, unprotected exposures of the eyes, in Macular Degeneration, to strong sunlight and to tobacco smoke, would limit benefits from an antioxidant used as a therapeutic agent for control of this disease. Therefore, one aspect of the invention provides synergistic therapies to patients by increasing antioxidant levels systemically or in specific organs as well as reducing oxidative, free radical generating and ionizing influences. In this case, glutathione therapy would be complemented with ultraviolet blocking sunglasses, and a tobacco smoking cessation plan, if necessary. A particularly advantageous antioxidant for combination with glutathione is alpha tocopherol succinate.

Free radicals occur in different parts or subparts of tissues and cells, with different inciting agents. For example, in trauma to the brain or spinal cord, the injurious free radicals are in the fatty (lipid) coverings that insulate nerve fibers, the myclin sheaths. Extremely high doses of a synthetic corticosteroid, 5 to 10 grams of methyl prednisolone sodium succinate (MPSS), given for just 24 hours, rapidly reach the brain and spinal cord and diffuse rapidly into the myelin, neutralizing the trauma-induced radicals, specifically: •OH, •OOH, and RO•. It is therefore an object of the invention to provide a pharmaceutical composition comprising a combination of glutathione and a glucocorticoid agent.

The accepted, published, peer-reviewed literature has repeatedly demonstrated the multiple properties of glutathione in the body. The abundant physiological and biochemical properties of glutathione led others into an extensive series of clinical trials wherein precursors of glutathione were administered, because the prevailing belief was that glutathione itself could not be effectively absorbed if it was simply given as glutathione. Hence, the popularity of the relatively ineffective and potentially damaging glutathione precursor N-acetyl cysteine (NAC) is currently being misused in the homosexual (high AIDS risk) community. The further belief was that glutathione would not cross the membranes of lymphocytes and other cells, whereas NAC could. The view was that to try to correct the glutathione deficiency in HIV/AIDS, with glutathione itself, was a hopeless task, because it would be degraded before uptake across membranes. However, the precursors of glutathione have failed to raise intracellular GSH levels. The present invention provides a suitable regimen to orally administer glutathione to achieve high bioavailability and increased intracellular levels of glutathione.

While prior studies have employed glutathione dissolved in orange juice to administer glutathione to AIDS patients, resulting in glutathione uptake, this method does not provide the advantages of an encapsulated or pill form, and there was no recognition for the need to prevent digestive dilution or glutathione derived impurities from being present.

Glutathione has also proven to be an effective anti-viral agent and interferes with HIV replication at a critical site that is not affected by other current drugs, viral mRNA transcription. Glutathione keeps viral DNA quiescent, especially when potent activators are present, like NFκB, and TNFα. Glutathione's anti-viral target appears to be at a point where the virus can not readily mutate. The dependence of HIV replication on binding activated NFκB onto its Long, Terminal Repeat (LTR) appears to be central to the virus.

According to the present invention, orally administered glutathione can safely raise cell levels beyond correcting glutathione deficiencies. A number of pathologic processes can be inhibited by these higher levels, for example, curtailing the virtually self-perpetuating, powerful biochemical cycles producing corrosive free radicals and toxic cytokines that are largely responsible for the signs and symptoms of AIDS. These biochemical cycles destroy considerable quantities of glutathione but they can eventually be brought under control, and nomialized with sufficient, on-going glutathione therapy. A typical example is the over production of a substance, 15 HPETE (15-hydroperoxy eicosatetraenoic acid), from activated macrophages. The 15 HPETE is a destructive, immunosuppressing substance and requires glutathione for conversion into a non-destructive, benign molecule. The problem is that once macrophages are activated, they're difficult to normalize.

Once inside cells, GSH curtails the production of free radicals and cytokines, corrects the dysfunctions of lymphocytes and of macrophages, reinforces defender cells in the lungs and other organs, halts HIV replication in all major infected cell types, by preventing the activation of the viral DNA by precluding the activation of NFκB, inhibits the TAT gene product of HIV that drives viral replication, dismantles the gp120 proteins of the virus coat. These gp120 proteins are the projections of the virus that normally allow it to lock onto susceptible CD4+ cells thereby helping the spread of the virus to uninfected CD4+ cells. By disrupting the gp120 protein, glutathione offers a potential mode of preventing transmission not only to other cells in the patient, but perhaps in precluding transmission to others.

Besides classic antiviral or antiretroviral agents (reverse transcriptase inhibitors, protease inhibitors), a number of other therapies may be of benefit for AIDS patients, and the present invention provides combinations of glutathione with the following drugs: cyclosporin A, thalidomide, pentoxifylline, selenium, desferroxamine, 2L-oxothiazolidine, 2L-oxothiazolidine-4-carboxylate, diethyldithiocarbamate (DDTC), BHA, nordihydroguairetic acid (NDGA), glucarate, EDTA, R-PIA, alpha-lipoic acid, quercetin, tannic acid, 2'-hydroxychalcone, 2-hydroxychalcone, flavones, alpha-angelicalactone, fraxetin, curcunin, probucol, and arcanut (areca catechul).

Inflammatory responses are accompanied by large oxidative bursts, resulting in large numbers of free radicals. Therefore, glutathione may have application in the therapy for inflammatory diseases. Glutathione may advantageously reduce the primary insult a well as undesired aspects of the secondary response. According to the present invention, glutathione may be administered to patients suffering from an inflammatory disease process, such as arthritis or various types, inflammatory bowel disease, etc. The present invention also provides combination pharmaceutical therapy including glutathione and an analgesic or antiinflammatory agent, for example opiate agonists, glucocorticoids or nonsteroidal antiinflammatory drugs (NSAIDS), including opium narcotics, meperidine, propoxyphene, nalbuphine, pentazocine, buprenorphine, asprin, indomethacin, diflunisal, acetominophen, ibuprofen, naproxen, fenoprofen, piroxicam, sulindac, tolmetin, meclofenamate, zomepirac, penicillamine, phenylbutazone, oxyphenbutazone, chloroquine, hydroxychloroquine, azathiaprine, cyclophosphamide, levamisole, prednisone, prednisolone, betamethasone, triamcinolone, and methylprednisolone.

Glutathione may also hold benefit for the treatment of parotitis, cervical dysplasia, Alzheimer's disease, Parkinson's disease, aminoquinoline toxicity, genitamycin toxicity, puromycin toxicity, aminoglycoside nephrotoxicity, paracetamol, acetaminophen and phenacetin toxicity.

Glutathione need not be orally ingested in order to provide the beneficial effects noted. While the drug may be administered intravenously or parenterally, it may also be administered through mucous membranes, including sublingually, as a vaginal or rectal suppository, and by pulmonary inhaler, for topical applications to the alveolar surface cells of the lungs to enhance pulmonary protection against unusual pneumonias. Systemic administration of glutathione may be used to concentrate glutathione in lymph nodes, and lymphoid tissues.

Glutathione tends to be unstable in solution. Therefore, one aspect of the present invention provides a pharmaceutical administration apparatus providing a dual chamber distribution pouch, having a frangible interconnection, allowing mixing between an aqueous phase and a dry glutathione preparation. The aqueous phase may be, for example, a gel, cream or foam. Either pouch may also contain another pharmaceutical agent, as described above.

The present invention also provides a glutathione administration appliance, for delivering an effective dose of glutathione to an accessible mucous membrane, such as the oral, vaginal, urethral or anal cavities. A dry glutathione preparation, for example in a dehydrated gel, matrix or polymer, having a high surface area per unit volume ratio, is provided in a foil bag or pouch. The dehydrated mass includes glutathione, as well as an optional stabilizing agent, such as ascorbic acid. The dehydrated mass is hydrated by the mucosal membrane or by an externally applied fluid, and the glutathione is then present to protect the mucous membrane from viral infection.

The ability of glutathione to chemically dismantle the gp120 protein of HIV by chemically destroying structural disulfide bonds, indicates that transmission of the infection may be curtailed to sonie extent. If gp120 is dismantled, the virus can not lock onto CD4+ cells. The oral glutathione treatment of patients may suffice to dismantle gp120 of viruses from treated patients. The topical applications of glutathione to mucous membranes might possibly serve to protect a sex partner if unsafe sexual practices occur.

Another effect is seen when glutathione or nitroso-glutathione is placed in the male urethra. In this case, the glutathione or glutathione derivative is absorbed. The vasodilatory effects of nitroso-glutathione, which is formed by interaction of glutathione with nitric oxide or provided directly, vasodilates the penis, resulting in an erection. Thus, a urethral glutathione or nitroso-glutathione suppository has potential for the treatment of impotence.

Glutathione or a glutathione derivative may also be co-administered with yohimbine, an alpha-2 receptor blocker, providing a synergistic effect. Yohimbine has been established to treat male sexual dysfunction, (e.g., impotence), among other effects.

Glutathione may be administered to mucous membranes in the form of a liquid, gel, cream, jelly, absorbed into a pad or sponge. Administration may also be provided by a powder or suspension.

The effective delivery of intact, pharmaceutically stabilized, bioavailable reduced L-glutathione has been accomplished according to the present invention. By providing high-dose glutathione for the body's general use, diabetics having either form of the disease may be provided with ample supplies of glutathione. Correcting the glutathione deficiency and also raising the levels inside cells to the upper range of normal will help to delay, or prevent the complications of diabetes.

Glutathione, orally administered according to the present invention, in moderately high doses, one to five gm/day, may be able to affect the outcome of macular degeneration. The avidity with which the RPE cells take Lip glutathione indicates that they may have a critical role in ameliorating this disorder. Unlike rods and cones, RPE cells can divide and replenish themselves if allowed. If caught at an early stage, before significant losses of rods and cones, the condition may be halted and delayed possibly indefinitely.

Since glutathione is relatively non-toxic, it may be used liberally for its advantageous properties. According to one aspect of the invention, glutathione may be added to a viral contaminated fluid or potentially contaminated fluid to inactivate the virus. This occurs, for example, by reduction of critical viral proteins. According to a preferred embodiment, glutathione is added to blood or blood components prior to transfusion. The added glutathione is in the reduced form, and is added in a concentration of between about 100 micromolar to about 500 millimolar or to a solubility limit, whichever is lower, and more preferably in a concentration of about 10–50 millimolar.

The addition of glutathione to whole blood, packed red blood cells or other formed blood components (white blood cells, platelets) may be used to increase the shelf life and/or quality of the cells or formed components.

EXAMPLE 1

Reduced L-glutathione, a naturally-occurring water-soluble tripeptide (gamma-glutamyl-cysteinyl-glycine) is the most prevalent intracellular thiol in most biological systems. A preferred formulation of glutathione according to the present invention provides capsules for oral use containing 500 mg reduced L-glutathione, 250 mg USP grade crystalline ascorbic acid, and not more than 0.9 mg magnesium stearate, NF grade in an OO-type gelatin capsule.

EXAMPLE 2

The preferred regimen for treatment of humans with glutathione according to the present invention is the administration of between 1 and three grams per day, in two divided doses, between meals (on an empty stomach), of encapsulated, stabilized glutathione according to Example 1. The study detailed in Appendix B administered the glutathione to HIV infected, otherwise healthy males between 18 and 65, with CD4+ cell counts above 500, not on any other medications. As detailed in FIG. 1, clinical responses were seen in the PBM intracellular glutathione levels. Thus, at 1 hour after administration of a 1 gram bolus of encapsulated stabilized glutathione in two 500 mg capsules, a three-fold increase in glutathione was measured. It is noted that, since the human body produces large quantities of glutathione, the effects of external glutathione in individual cases may sometimes be masked or even appear paradoxical. However, as shown in FIG. 2, a statistical analysis shows a dose response effect of the administration of glutathione according to the present invention to the subject population.

EXAMPLE 3

FIG. 2 shows a graph from one of the 24 HIV positive people in the Company's Clinical Trial. The graph illustrates increases in the glutathione (GSH) content of immune system cells, in the blood, resulting from two doses of pharmaceutically stabilized GSH according to Example 1. The first dose of one gram was taken at 0 time, or 10:00 a.m. and the second dose at 3 hours, or 1:00 p.m. The baseline points were from two weeks earlier, on the same patient. A temporary intravenous catheter was in place for 7 hours to permit frequent blood sampling at the numerous time points. The units are in nanomoles of CSH per 10 million peripheral blood mononuclear cells (PBMC's). The graph is an example of the elevation of GSH inside PBMC's. The statistical analysis of the entire patient population shows statistically significant elevations and a significant dose response relationship.

In a compressed Phase I/II clinical trial (FDA IND#45012), in a well defined GSH deficiency state, HIV infection, the composition according to Example 1 administered according to the protocol of Example 2 was demonstrated to rapidly and safely raises intracellular GSH levels two to three fold. Thus, by employing the composition according to Example 1 administered according to the protocol of Example 2, an oral pharmaceutical has been shown to treat the critical losses of GSH that are known to propel a range of major disorders.

The glutathione metabolism, especially the pharmacokinetics, of the subjects of the Phase II study is believed to be relatively normal. Therefore, the same regimen may be applied in the treatment of other conditions, including CHF, diabetes, early stroke or other ischemic event, toxic insult, viral infection or disease, or other condition in which free radical reactions are uncontrolled, aberrant, or contribute to pathology.

EXAMPLE 4

Combination of Glutathione and Acetaminophen

A combination pharmaceutical is provided to ameliorate the detrimental effects of acetaminophen, a drug which consumes glutathione in the liver during metabolism, and in excess doses causes liver damage due to oxidative damage. The composition includes 500 mg L-glutathione, 250 mg crystalline ascorbic acid, and 350 mg acetaminophen.

EXAMPLE 5

Combination of Glutahione and Chlorpromazine

A combination pharmaceutical is provided to ameliorate the detrimental effects of chlorpromazine, a phenothiazine drug which causes side effects, including tardive dyskinesia, possibly relating to excess free radical reactions. The composition includes 500 mg L-glutathione, 250 mg crystalline ascorbic acid, and 200 mg chlorpromazine.

EXAMPLE 6

Combination of Glutathione and Aminoglycosides

A combination pharmaceutical is provided to ameliorate the detrimental effects of Aminoglycoside drugs, which include, but are not limited to, neomycin, kanamycin, amikacin, streptomycin, gentamycin, sisomicin, netilmicin and tobramycin, a drug class which may be associated with various toxicities. This damage may be related to oxidative damage or consumption of glutathione during metabolism. The composition according to the present invention is an intravenous formulation, including the aminoglycoside in an effective amount, and L-glutathione in an amount of about 10–20 mg/kg. Ascorbic acid in an amount of 5–10 mg/kg may be added as a stabilizer.

EXAMPLE 7

Urethral Insert

A composition containing 200 mg glutathione, 50 mg ascorbic acid per unit dosage is mixed with carageenan and/or agarose and water in a quick-gelling composition, and permitted to gel in a cylindrical form having a diameter of about 3 mm and a length of about 30 mm. The composition is then subjected to nitric oxide to cause between 0.1–10% of the glutathione to be converted to nitroso-glutathione. The gelled agarose is then freeze dried under conditions which allow shrinkage. The freeze dried gel is than packaged in a gas barrier package, such as a foil pouch or foil "bubble-pack".

The freeze dried gel may then be used as a source of nitroso-glutathione for administration transmucosally. The cylindrical freeze dried gel may be inserted into the male urethra for treatment of impotence, or administered sublingually for systemic vasodilation.

EXAMPLE 7

Vascular Disease Prophylaxis

An oral formulation is provided for prophylaxis of vascular disease, e.g., in men over 40. The composition includes 500 mg reduced L-glutathione, 250 mg USP grade crystalline ascorbic acid, and 50 mg USP acetyl salicylic acid (aspirin) in an OO-type gelatin capsule. Typical administration is twice per day.

Advantageously, the acetyl salicylic acid may provided in enteric release pellets within the capsule, slowing release.

EXAMPLE 8

Vascular Disease Prophylaxis

Arginine is the normal starting substrate for the production of nitric oxide. Arginine is normally in limited supply, and thus a relative deficiency of arginine may result in impaired vascular endothelial function.

An oral formulation is provided for prophylaxis of vascular disease. The composition includes 500 mg reduced L-glutathione, 200 mg USP grade crystalline ascorbic acid, and 200 mg arginine, in an O-type gelatin capsule.

EXAMPLE 9

Vascular Disease Prophylaxis

Vitamin E consumption reduces the risk of heart attack and other vascular disease. Vitamin E succinate (alpha-tocopherol succinate) is a dry powder.

An oral formulation is provided for prophylaxis of vascular disease. The composition includes 500 mg reduced L-glutathione, 200 mg USP grade crystalline ascorbic acid, and 200 mg vitamin E succinate, in an OO-type gelatin capsule.

EXAMPLE 10

Vascular Disease Prophylaxis

Nonspecific esterases are present in the plasma which have a broad substrate specificity. According to the present invention, esters are formed between agents which are useful combination therapies, in order to provide for efficient administration, high bioavailability, and pharmaceutical stability. Preferred esters include alpha tocopherol-ascorbate, alpha tocopherol-salicylate, and ascorbyl-salicylate. The tocopherol ester maintains the molecule in a reduced state, allowing full antioxidant potential after ester cleavage.

These esters may be administered alone or in combination with other agents, for example glutathione. Typically, these are administered to deliver an effective dose of salicylate equivalent of 100 mg per day for prophylaxis or 750–1000 mg per dose for treatment of inflammatory diseases. Tocopherol is administered in an amount of 100–500 IU equivalent. Ascorbate is administered in an amount of up to 1000 mg equivalent.

In order to enhance availability, a non-specific esterase may be provided in the formulation to cleave the ester after dissolution of the capsule. Therefore, a non-specific esterase, such as a bacterial or saccharomyces (yeast) enzyme or enriched enzyme preparation may be included in the formulation, such as included as a powder or as pellets in the capsule.

EXAMPLE 11

Vascular Disease Prophylaxis

Nordihydroguaretic acid is a known lipoxygenase inhibitor. This composition may therefore be used to treat inflammatory processes or as prophylaxis against vascular disease.

An oral formulation is provided for prophylaxis of vascular disease. The composition includes 500 mg reduced L-glutathione, 200 mg USP grade crystaline ascorbic acid, and 100 mg nordihydroguaretic acid, in an OO-type gelatin capsule. Typical administration is twice per day.

It should be understood that the preferred embodiments and examples described herein are for illustrative purposes only and are not to be construed as limiting the scope of the present invention, which is properly delineated only in the appended claims.

REFERENCES

Each of the following references is incorporated herein in its entirety:

Glutathione, General

Aruga, M., Awazu, S. and Hanano, M.: Kinetic studies on the decomposition of glutathione. I. Decomposition in solid state. Chem. Pharm. Bull. 26:2081–91, 1978.

Aruga, M., Awazu, S. and Hanano, M.: Kinetic studies on decomposition of glutathione. II. Anaerobic decomposition in aqueous solution. Chem. Pharm. Bull. 28:514–20, 1980.

Aruga, M., Awazu, S. and Hanano, M.: Kinetic studies on decomposition of glutathione. III. Peptide bond cleavage and desulfurization in aqueous solution. Chem. Pharm. Bull. 28:521–28, 1980.

Hagen, T. M., Aw, T. Y., and Jones, D. P.: Glutathione uptake and protection against oxidative injury in isolated kidney cells. Kidney Intl. 34:74–81, 1988.

Lash. L. H., and Jones, D. P.: Distribution of oxidized and reduced forms of glutathione and cysteine in rat plasma. Arch. Biochem. Biophys. 240:583–92, 1985.

Meister, A.: Selective modification of glutathione metabolism. Science 220:472–477, 1983.

Meister, A. and Anderson, M. E.: Glutathione. Ann. Rev. Biochem. 52:711–60, 1983.

Riley, R. J., Spielberg, S. P., Leeder, J. S.: A comparative study of the toxicity of chemically reactive xenobiotics towards adherent cell cultures: selective attenuation of menadione toxicity by buthionine sulphoximine pretreatment. J. Pharmacol. 45(4): 263–267, 1993.

Wierzbicka, G. T., Hagen, T. M. & Jones, D. P.: Glutathione in food. J. Food Comp. Anal. 2:327–337, 1989.

Glutathione and the Immune System

Dröge, W., Pottmeyer-Gerber, C., Schmidt, H. & Nick, S.: Glutathione augments the activation of cytotoxic T lymphocytes in vivo. Immunobiol. 172:151–156, 1986.

Droge, W., Eck, H. P., Gmunder, H., and Mihm, S.: Modulation of lymphocyte functions and immune responses by cysteine and cysteine derivatives. Amer. J. Medicine 91(3C):140S–144S, 1991.

Furukawa, T., Meydani, S. N. & Blumberg, J. B.: Reversal of age-associated decline in imnmune responsiveness by dietary glutathione supplementation in mice. Mech. Ageing, Dev. 38:107–117, 1987.

Franklin, R. A., Yong, M. L., Arkins, S., and Kelley, K. W.: Glutathione augments in vitro proliferative responses of lymphocytes to concanavalin A to a greater degree in old than in young rats. J. Nutr. 120:1710–17, 1990.

Kavanaugh, T. J., Grossman, A., Jaecks, E. P, Jinneman, J. C., Eaton, D. L., Masrtin, G. M., and Rabinovitch, P. S.: Proliferative capacity of human peripheral lymphocytes sorted on the basis of glutathione content. J. Cell. Physiol. 145:472–80, 1990.

Robinson, M. K, Rodrick, M. L., Jacobs, D. O., Rounds, J. D., Collins, K. H., Saproschetz, I. B., Mannick, J. A., and Wilmore, D. W.: Glutathione depletion in rats impairs T-cell and macrophage immune function. Arch. Surg. 128:29–35, 1993.

Suthanthiran, M., Anderson, M. E., Sharma, V. K. & Meister, A.: Glutathione regulates activation-dependent DNA synthesis in highly purified normal human T lymphocytes stimulated via the CD2 and CD3 antigens. Proc. Natl. Acad. Sci. USA 87:3343–3347, 1990.

Glutathione as a Detoxicant

Bravenboer, B., Kappelle, A. C., Hamers, F. P., van Buren, T., Erkelens, D. W. & Gispen, W. H.: Potential use of glutathione for the prevention and treatment of diabetic neuropathy in the streptozocin-induced diabetic rat. Diabetologia 35:813–817, 1992.

Cavaletti, E., Tofanetti, O. & Zunino F.: Comparison of reduced glutathione with 2-mercaptoethane sulfonate to prevent cyclophosphamide-induced urotoxicity. Cancer Letters 32:1, 1986.

Hamers, F. P., Brakkee, J. H., Cavalletti, E., Tedeschi, M., Marmonti, L., Pezzoni, G., Neijt, J. P. & Gispen, W. H.: Reduced glutathione protects against cisplatin-induced neurotoxicity in rats. Cancer Res. 53:544–549, 1993.

Kromidas, L., Trombetta, L. D., and Jamall, I. S.: The protective effects of glutathione against methylmercury cytotoxicity. Toxicol. Letters 51:67–80, 1990.

Novi, A. M., Flohe, R., and Stukenkemper, S.: Glutathione and aflatoxin $B_1$-induced liver tumors: requirement for an intact glutathione molecule for regression of malignancy in neoplastic tissue. Ann. NY Acad. Sci. 397:62–71, 1982.

Rao, R. D. N., Fischer, V., and Mason, R. P.: Glutathione and ascorbate reduction of the acetaminophen radical formed by peroxidase. J. Biol. Chem. 265:844–7, 1990.

Skoulis, N. P., James, R. C., Harbison, R. D. and Roberts, S. M.: Depression of hepatic glutathione by opioid analgesic drugs in mice. Toxicol. Appl. Pharmacol. 99:139–47, 1989.

Villani, F., Galimberti, M., Zunino, F., Monti, F., Rozza, A., Favalli, L. & Poggi, P.: Prevention of doxorubicin-induced cardiomyopathy by reduced glutathione. Cancer Chemother. Pharmacol. 28:365–369, 1991.

Wagner, G., Frenzel, H., Wefers, H. and Sies, H.: Lack of effect of long-term glutathione administration on aflatoxin B1-induced hepatoma in male rats. Chem. Biol. Interactions 53:57–68, 1985.

Yoda, Y., Nakazawa, M., Abe, T & Kawakami, Z.: Prevention of Doxorubicin myocardial toxicity in mice by reduced glutathione. Cancer Research 46:2551, 1986.

Younes, M., and Strubelt, O.: Protection by exogenous glutathione against hypoxic and cyanide-induced damage to isolated perfused rat livers. Toxicol. Letters 50:229–236, 1990.

McCartney, M. A.: Effect of glutathione depletion on morphine toxicity in mice. Biochem. Pharmacol. 38:207–9, 1989.

Ishida, T., Kumagai, Y., Ikeda, Y., Ito, K., Yano, M., Toki, S., Mihashi, K., Fujioka, T., Iwase, Y. and Hachiyama, S.: (8S)-(glutathione-S-YL)dihydromorphinone, a novel metabolite kof morphine from guinea pig bile. Drug. Metab. Dispos. 17:77–81, 1989.

Nagamatsu, K., Kido, Y., Teroa, T, Ishida, T. and Toki, S.: Protective effect of sulfhydryl compounds on acute toxicity of morphinone. Life Sci. 30:1121–27, 1982.

Glutathione as an Adjunct to Cancer Chemotherapy

Bohm, S., Battista-Spatti, G., DiRe, F., Oriana, S., Pilotti, S., Tedeschi, M., Tognella, S. & Zunino, F.: A feasibility study of cisplatin administration with low-volume hydration and glutathione protection in the treatment of ovarian carcinoma. Anticancer Res. 11:1613–1616, 1991.

Cozzaglio, L., Doci, R., Colla, G., Zunino, F., Casciarri, G. & Gennari, L.: A feasibility study of high-dose cisplatin and 5-fluorouracil with glutathione protection in the treatment of advanced colorectal cancer. Tumori 76:590–594, 1990.

Di Re, F., Bohm, S., Oriana, S., Spatti, G. B., & Zunino, F.: Efficacy and safety of highi-dose cisplatin and cyclophosphamide with glutathione protection in the treatment of bulky advanced epithelial ovarian cancer. Cancer Chemother. Pharmacol. 25:355–360, 1990.

Nobile, M. T., Vidili, M. G., Benasso, M., Venturini, M., Tedeschi, M., Zunino, F., & Rosso, R.: A preliminary clinical study of cyclophosphamide with reduced glutathione as uroprotector. Tumori 75:257–258, 1989.

Glutathione use in Patients with Abnormal Glucose Tolerance, and with Diabetes

Ceriello, A., Giugliano, D., Quatraro, A. & Lefebvre, P. J.: Anti-oxidants show an anti-hypertensive effect in diabetic and hypertensive subjects. Clin. Sci. 81:739–742, 1991.

Paolisso, G., Giugliano, D., Pizza, G., Gambardella, A., Tesauro, P., Varricchio, M. & D'Onofrio, F.: Glutathione infusion potentiates glucose-induced insulin secretion in aged patients with impaired glucose tolerance. Diabetes Care 15:1–7, 1992.

Glutathione as a Treatment for Renal Failure

Costagliola, C., Romano, L., Scibelli, G., de Vincentiis. A., Sorice, P. & DiBenidetto, A.: Anemia and chronic renal failure: a therapeutic approach by reduced glutathione parenteral administration. Nephron 61:404–408, 1992.

Toxicological Effects of Glutathione

Dalhoff, K., Ranek, L., Mantoni, M. & Poulsen, H. E.: Glutathionie treatment of hepatocellular carcinoma. Liver 12:341–343, 1992.

Dekant, W.: Bioactivation of nephrotoxins and renal carcinogens bv glutathion4 S-conjugate formation. Toxicol. Letters 67:151–60, 1993.

Domingo, J. L.. Gomez, M., Llobet, J. M. & Corbella, J.: Chelating agents in the treatment of acute vanadyl sulphate intoxication in mice. Toxicology 62: 203–211, 1990.

Martensson, J., Han, J., Griffith, O. W. & Meister, A.: Glutathione ester delays the onset of scurvy in ascorbate-deficicient guinea pigs. Proc. Nat. Acad. Sci. USA 90:317–321, 1993.

Thust, R, and Bach, B.: Exogenous glutathione induces sister chromatid exchanges, clastogenicity and endoreduplication in V79-E Chinese hamster cells. Cell Biol. Toxicol. 1:123–31, 1985.

HIV Infection

Arpadi, S. M., Zang, E, Muscat J. and Richie, J.: Glutathione deficiency in HIV-1-infected children with growth failure, (submitted for publication).

Baker, D. H. and Wood, R. J.: Cellular antioxidant status and human immunodeficiency virus replication. Nutr. Rev. 50:15–8, 1992.

Baruchel, S., and Wainberg, M. A.: The role of oxidative stress in disease progression in individuals infected by the human immunodeficiency virus. J. Leukocyte Biol. 52:111–114, 1992.

Buhl, R., Holroyd, K. J., Mastrangli, A., Cantin, A. M., Jaffe, H. A., Wells, F. B., Saltini, C. and Crystal, R. G.: Systemic glutathione deficiency in symptom-free HIV-seropositive individuals. Lancet ii:1294–1298, 1989.

de Quay, B., Malinverni, R. and Lauterburg, B. H.: Glutathione depletion in HIV-infected patients: role of cysteine deficiency and effect of oral N-acetylcysteine. AIDS 6:815–9, 1992.

Droge, W., Eck, H. P. and Mihm, S.: HIV-induced cysteine deficiency and T-cell dysfunction—a rationale for treatment with N-acetylcysteine. Immunol. Today 13:211–4, 1992.

Eck, H. P., Gmunder, H., Hartmann, M., Petzoldt, D., Daniel, V. and Droge, W.: Low concentrations of acid-soluble thiol (cysteine) in the blood plasma of HIV-1-infected patients. Biol. Chem. Hoppe-Seyler 370:101–108, 1989.

Fauci, A. S.: Multifactorial nature of human immunodeficiency virus disease: Implications for therapy. Science 262:1011–1018, 1993.

Foley, P. Kazazi, F., Biti, R., Sorrell, T. C., and Cunningham, A. L.: HIV infection of monocytes inhibits the T-lymphocyte proliferative response to recall antigens via production of eicosanoids. Immunology 75:391–97, 1992.

Hasan, V., Thomas, D., Aclami, J. et al.: Stimulation of a human T-cell clone with anti-CD3 or tumor necrosis factor induces NFκB translocation but not human immunodeficiency virus 1 enhancer-dependent transcription. Proc. Natl. ACAD. sCI. 87:7861–65, 1990.

Ho, W. Z. and Douglas, S. D.: Glutathione and N-acetylcysteine suppression of human immunodeficiency virus replication in human monocyte/macrophagcs in vitro. AIDS Res. Hum. Retroviruses, 8:1249–53, 1999.

Israel, N., Gougerot-Pocidalo, M. A., Aillet, F., and Virelizier, J. L.: Redox status of cells influences constitutive or induced NFκB translocation and HIV long, terminal repeat activity in human T and monocytic cell lines. J. Immunol. 149:3386–93, 1992.

Kobayashi, S., Hamamoto, Y., Kobayashi, N., and Yamamoto, N.: Serum level of TNFa in HIV-infected individuals. AIDS 4:169 1990.

Kalebic, T., Kinter, A., Poli, G., Anderson, M. E., Meister, A. and Fauci, A. S.: Suppression of human immunodeficiency virus expression in chronically infected monocytic cells by glutathione, glutathione ester, and N-acetylcysteine. Proc. Natl. Acad. Sci. USA 87:986–990, 1991.

LeGrand-Poels, S., Vaira, D., Pincemail, J., Van de Vorst, A. and Piette, J.: Activation of human immunodeficiency virus type 1 by oxidative stress. AIDS Res. Hum. Retrov. 6:1389–97, 1990.

Mihan, S., Ennen, J., Pessara, U., Kurth, R. and Droge, W.: Inhibition of HIV-1 replication and NF-kb activity by cysteine and cysteine derivatives. AIDS 5:497–503, 1991.

National Institutes of Health. Dr. Howard C. Greenspan, Chairman of Conference on Free Radicals and Antioxidants in HIV/AIDS, Nov. 12–13, 1993/Greenspan, H. C. The role of reactive oxygen species, antioxidants and phytopharmaceuticals in human immunodeficiency virus activity. Med-Hypotheses 40:85–92, 1993.

Roederer, M., Raju, P. A., Staal, F. J. T., Herzenberg, L. A. and Herzenberg, L. A.: N-acetylcysteine inhibits latent HIV expression in chronically infected cells. AIDS Res. Human Retrovir. 7:(6) 563–567, 1991.

Roederer, M., Staal, F. J. T., Osada, H., Herzenberg, L. A. and Herzenberg, L. A.: CD4 and CD8 T cells with high intracellular glutathione levels are selectively lost as the HIV infection progresses. Internat. Immunol 3:933–37, 1991.

Roederer, M., Staal, F. J. T., Raju, P. A., Ela, S. W., Herzenberg, L. A. and Herzenberg, L. A.: Cytokine-stimulated human immunodeficiency virus replication is inhibited by N-acetyl-L-cysteine. Proc. Natl. Acad. Sci. USA 87:4884–4888, 1990.

Schreck, R. Rieber, P., and Baeurle, P. A.: Reactive oxygen intermediates as apparently widely used messengers in the activation of the NF-kb transcription factor and HIV-1. EMBO J. 10:2247–2258, 1991.

Staal, F. J., Roederer, M., Herzenberg, L. A. and Herzenberg, L. A.: Glutathione and immunophenotypes of T and B lymphocytes in HIV-infected individuals. Ann. NY Acad. Sci. 651:453–63, 1992.

Staal, F. J. T., Roederer, M. Herzenberg, L. A., and Herzenberg, L. A.: lntracellular thiols regulate activation of nuclear factor kappa-B and transcription of human immunodeficiency virus. Proc Natl. Acad. Sci. USA 87:9943–9947, 1990.

Staal, F. J., Ela, S. W., Roederer, M., Anderson, M. T., Herzenberg, L. A. and Herzenberg, L. A.: Glutathione deficiency and human immunodeficiency virus infection. Lancet 339:909–12, 1992.

Staal, F. J., Roederer, M., Israelski, D. M., Bubp, J., Mole, L. A., McShane, D., Deresinski, S. C., Ross, W., Sussman, H., Raju, P. A., Herzenberg,, L. A. and Herzenberg, L. A.: Intracellular glutathione levels in T cell subsets decrease in HIV-infected individuals. AIDS Res. Hum. Retroviruses 8:305–11, 1992.

Staal, F. J. T., Roederer, M., Raju, P. A., Anderson, M. T., Ela, S. W., Herzenberg, L. A., and Herzenberg, L. A.: Antioxidants inhibit stimulation of HIV transcription. AIDS Res. Hum. Retrov. 9:299–306, 1993.

Wahl, L. M., Corcoran, M. L., Pyle, S. W., Arthur, L. O., Harel-Bellan, A. and Farrar, W. L.: Human immunodeficiency virus glycoprotein (gp120) induction of monocyte arachidonic acid metabolites and interleukin 1. Proc. Natl. Acad. Sci. 86:621–625, 1989.

Measurement of Glutathione

Fahey, R. C., and Newton, G. L.: Determination of low molecular weight thiols using monobromobimane fluorescent labeling, and high-performance liquid chromatography. Meth. Enzymol. 143:85–96, 1987.

Mills, B. J., Richie. J. P. Jr., and Lang, C. A.: Sample processing alters glutathione and cysteine values in blood. Anal. Biochem. 184:263–267, 1990.

Richie, J. P. Jr., and Lang. C. A.: The determination of glutathione, cyst(e)ine, and other thiols and disulfides in biological samples using high-performance liquid chromatography with dual electrochemical detection. Anal. Biochem. 163:9–15, 1987.

Tietz, F.: Enzymic method for quantitative determination of nanogram amounts of total and oxidized glutathione: Applications to mammalian blood and other tissues. Anal. Biochem. 27:502–22, 1969.

Pharmacokinetics and Biological Disposition of Glutathione in Animals

Aebi, S. & Lauterberg, B. H.: Divergent effects of intravenous GSH and cysteine on renal and hepatic GSH. Acr. J. Physiol. 263(2 pt 2):R348-R352, 1992.

Ammon, H. P. T., Melien, M. C. M. & Verspohl, E. J.: Pharmacokinetics of intravenously administered glutathione in the rat. J. Pharm. Pharmacol. 38:721–725, 1986.

Anderson, M. E., Powrie, F., Puri. R. N., & Meister, A.: Glutathione monoethyl ester: Preparation, uptake by tissues, and conversion to glutathione. Arch. Biochem. Biophys. 239:538–548, 1985.

Aw, T. Y., Wierzbicka, G. & Jones, D. P.: Oral glutathione increases tissue glutathione in vivo. Chem. Biol. Interact. 80:89–97, 1991.

Borok, Z., Buhl, R., Grimes, G. J., Bokser, A. D., Hubbard, R. C., Holroyd, K. J., Roum, J. H., Czerski, D. B., Cantin, A. M., & Crystal, R. G.: Effect of glutathione aerosol on oxidant-antioxidant imbalance in idiopathic pulmonary fibrosis. The Lancet 338:215–216, 1991.

Buhl, R., Vogelmeier, C., Critenden, M., Hubbard, R. C., Hoyt, Jr., R. F., Wilson, E. M., Cantin, A. M. & Crystal, R. G.: Augmentation of glutathione in the fluid lining the epithelium of the lower respiratory tract by directly administering glutathione aerosol. Proc. Natl. Acad. Sci. USA 87: 4063–4067, 1990.

Bump, E. A., al-Sarraf, R., Pierce, S. M. & Coleman, C. N.: Elevation of mouse kidney thiol content following administration of glutathione. Radiother. Oncol. 23:21–25, 1992.

Griffith, O. W., Bridges, R. J., & Meister, A.: Formation of g-glutamyl-cyst(e)ine in vivo is catalyzed by g-glutamyl transpeptidase. Proc. Natl. Acad. Sci. USA 78:2777–2781, 1981.

Hagen, T. M., Wierzbicka, G. T., Bowman, B. B., Aw, T. Y. & Jones, D. P.: Fate of dietary glutathione. Disposition in the gastrointestinal tract. Am. J. Physiol. 259: G530-G535, 1990.

Hagen, T. M. & Jones. D. P.: Transepithelial transport of glutathione in vascularly perfused small intestine of rat. Am. J. Physiol. 252:G607-G613, 1987.

Hagen, T. M., Wierzbicka, G. T., Sillau, A. H., Bowman, B. B. & Jones, D. P.: Bioavailability of dietary glutathione. Effect on plasma concentration. Am. J. Physiol. 259:G524-G529, 1990.

Hahn, R., Wendel, A. & Flohé, L.: The fate of extracellular glutathione in the rat. Biochim. Biophys. Acta 539:324–337, 1978.

Puri, R. N., & Meister, A.: Transport of glutathione, as g-glutamylcysteinylglycyl ester, into liver and kidney. Proc. Natl. Acad. Sci. USA 80:5258–5260, 1983.

Viña, J., Perez, C., Furukawa, T., Palacin, M. & Viña, J. R.: Effect of oral glutathione on hepatic glutathione levels in rats and mice. Brit. J. Nutr. 62:683–91, 1989.

Pharmacokinetics of Glutathione in Humans

Aebi, S., Asserto, R., & Lauterberg, B. H.: High-dose intravenous glutathione in man.: Pharmacokinetics and effects on cyst(e)ine levels in plasma and urine. Eur. J. Clin. Invest. 21:103–110, 1991.

Hagen, T. M. and Jones, D. P. Role of glutathione transport in extrahepatic detoxication. in Glutathione Centennial: Molecular Perspectives and Clinical Implications, N. Taniguchi, T. Higashi, Y. Sakamoto and A. Meister, eds. Acad. Press, New York, 1990.

Jones, D. P., Hagen, T. M., Weber, R., Wierzbicka, G. T., and Bonkovsky, H. L.: Oral administration of glutathione (GSH) increases plasma GSH concentration in humans. FASEB J. 3:A1250 (5953), 1990.

Inflammation

Kuehl, F. A., Ham, E. A., Egan, R. W., Dougherty, H. W., Bonney, R. J. and Humes, J. L.: Studies on a destructive oxidant released in the enzymatic reduction of prostaglandin G2 and other hydroperoxy acids. In: Pathology of Oxygen, ed. A. P. Auton, Acad. Press, New York, 1982, pp. 175–190.

Lash, L. H., Hagen, T. M., & Jones, D. P.: Exogenous glutathione protects intestinal epithelial cells from oxidative injury. Proc. Natl. Acad. Sci. USA 83:4641–4645, 1986.

Vascular Effects of Glutathione

Demopoulos, H. B., Flamm, E. S., Pietronigro, D. D., and Seligman, M. L.: Free radical pathology and antioxidants in regional cerebral ischemia and central nervous system trauma. In: Anesthesia and Neurosurgery, eds. J. E. Cottrell and H. Tunndorf. C. V. Mosby, St. Louis, 1986, pp. 246–279.

Kagan, V. E., Bakalova, R. A., Koynova, G. M., Tyurin, V. A., Seriniva, E. A., Petkov, V. V., Staneva, D. S. and Packer, L.: Antioxidant protection of the brain against oxidative stress. In: Free Radicals in the Brain., eds. L. Packer, L. Prilipko, and Y. Christen. Springer-Verlag, New York, 1992, pp. 49–61.

Pietronigro, D. D., Demopoulos, H. B., Hovsepian, M. and Flamm, E. S.: Brain ascorbic acid depletion during cerebral ischemia. Stroke 13:117–119, 1982.

Shan, X., Aw, T. Y. and Jones, D. P.: Glutathione-dependent protection against oxidative injury. Pharmac. Ther. 47:61–71, 1990.

Simon, D. I., Stamler, J. S., Jaraki, O., et al.: Antiplatelet properties of protein S-nitrosothiols derived from nitric oxide and endothelium-derived relaxing factor. Arterioscler. Thromb. 13(6):791–799, 1993.

Taccone-Gallucci, M., Lubrano, R., Clerico, A., Meloni, C., Morosetti, M., Meschini, L., Elli, M., Trapasso, E., Castello, M. A. & Casciani, C. U.: Administration of GSH has no influence on the RBC membrane: Oxidative damage to patients on hemodialysis. ASAIO Journal 38:855–857, 1992.

Miscellaneous

Lenzi, A., Lombardo, F., Gandini, L., Culasso, F. & Dondero, F.: Glutathione therapy for male infertility. Arch. Androl. 29:65–68, 1992.

What is claimed is:

1. An pharmaceutical formulation, comprising Glutathione, in combination with an effective amount of one or more of a pharmaceutically acceptable physiologic nitric oxide precursor, and an antimicrobial composition.

2. The formulation according to claim 1, wherein the formulation acts as a vasodilator through alteration of nitric oxide metabolism.

3. The formulation according to claim 1, wherein the formulation is effective for treating pathological vasospasm.

4. The formulation according to claim 1, wherein the formulation is effective for treating sexual dysfunction.

5. The formulation according to claim 1, in combination with a drug effective to treat congestive heart failure.

6. The formulation according to claim 1, wherein said formulation is in unit dosage form and comprises in physiologic nitric oxide precursor.

7. The formulation according to claim 6, wherein the nitric oxide precursor is arginine.

8. The formulation according to claim 6, wherein said formulation comprises about 500 mg reduced L-glutathione, about 200 mg ascorbic acid, and about 200 mg arginine.

9. The formulation according to claim 1, wherein the formulation comprises a nitric oxide precursor and an antiviral composition.

10. The formulation according to claim 1, wherein the nitric oxide precursor comprises an $NO_2$ functionality.

11. The formulation according to claim 10, wherein the nitric oxide precursor comprises an organic nitrate.

12. The formulation according to claim 1, wherein said formulation comprises a pharmacutically acceptable antimicrobial antibiotic agent.

13. The formulation according to claim 1, wherein said antimicrobial compostion comprises an antimicrobial having activity against mycoplasma infection.

14. The formulation according to claim 1, wherein said antimicrobial agent comprises an antibiotic in sufficient amount to suppress growth of a microbe and said glutathione is provided in sufficent amount to control free radical reactions associated with the microbe.

15. The pharmaceutical formulation according to claim 1, wherein said formulation is provided in an oral dosage form.

16. The formulation according to claim 1, wherein said antimicrobial compostion comprises an aminoglycoside.

17. The formulation according to claim 1, wherein said antimicrobial compostion comprises a quinolone antibiotic.

18. The formulation according to claim 1, wherein said formulation is adapted to modify vascular tone in an organism administered said formulation.

19. A pharmaccutical composition comprising in combination glutathione, or a pharmaccutically acceptable salt or derivative thereof, and an antiviral or antimicrobial antibiotic agent, said glutathione being present in an effective amount to at least one of: serve as an efffective antioxidant agent; supplement endogenous glutathione consumed as a result of administration of the pharmaccutical composition; alter cardiovascular status of a host; alter a redox status of a bost; and alter a gene expression within a host, and said antimicrobial agent being present in an effective amount to treat or prophylax a microbial-associated condition of the host.

20. The pharmaceutical composition according to claim 19, comprising, in unit dosage form, glutathione in an amount of at least 250 mg., a sacrificial antioxidant to preserve the glutathione in a reduced state, an effective amount of a pharmaceutically acceptable topoisomerase inhibitor, and a pharmaceutically acceptable physiologic nitric oxide precursor.

21. The pharmaceutical composition according to claim 19, wherein the antioxidant comprises ascorbic acid.

22. The pharmaceutical composition according to claim 19, further comprising an antibiotic having activity against mycoplasma infection.

23. The pharmaceutical composition according to claim 19, wherein said composition is provided in an oral dosage form.

24. The pharmaceutical composition according to claim 19, comprising an aminoglycoside antibiotic.

25. The pharmaceutical composition according to claim 19, comprising a quinolone antibiotic.

* * * * *